(12) United States Patent
Kato et al.

(10) Patent No.: US 11,630,221 B2
(45) Date of Patent: Apr. 18, 2023

(54) RADIATION DETECTOR, RADIOGRAPHIC IMAGING DEVICE, AND MANUFACTURING METHOD

(71) Applicant: FUJIFILM Corporation, Tokyo (JP)

(72) Inventors: Munetaka Kato, Kanagawa (JP); Shinichi Ushikura, Kanagawa (JP); Yoshihiro Okada, Kanagawa (JP); Keiichi Akamatsu, Kanagawa (JP); Haruyasu Nakatsugawa, Kanagawa (JP)

(73) Assignee: FUJIFILM Corporation, Tokyo (JP)

(\*) Notice: Subject to any disclaimer, the term of this patent is extended or adjusted under 35 U.S.C. 154(b) by 363 days.

(21) Appl. No.: 17/025,621

(22) Filed: Sep. 18, 2020

(65) Prior Publication Data

US 2021/0003722 A1 Jan. 7, 2021

Related U.S. Application Data

(63) Continuation of application No. PCT/JP2019/009428, filed on Mar. 8, 2019.

(30) Foreign Application Priority Data

Mar. 19, 2018 (JP) .............................. JP2018-051690
Sep. 27, 2018 (JP) .............................. JP2018-182730

(Continued)

(51) Int. Cl.
  *G01T 1/20* (2006.01)
  *H01L 27/146* (2006.01)
  (Continued)

(52) U.S. Cl.
  CPC ............ *G01T 1/20188* (2020.05); *A61B 6/00* (2013.01); *A61B 6/4208* (2013.01);
  (Continued)

(58) Field of Classification Search
  CPC ..... A61B 6/00; A61B 6/4208; G01T 1/20181; G01T 1/20188; G01T 1/2023; G01T 1/208; G01T 7/00; H01L 27/14661
  See application file for complete search history.

(56) References Cited

U.S. PATENT DOCUMENTS

2006/0038132 A1 2/2006 Hayashida
2010/0193691 A1 8/2010 Ishii et al.
(Continued)

FOREIGN PATENT DOCUMENTS

JP 2006-058124 A 3/2006
JP 2009-133837 A 6/2009
(Continued)

OTHER PUBLICATIONS

International Search Report issued in PCT/JP2019/009428; dated Jun. 4, 2019.
(Continued)

*Primary Examiner* — Mark R Gaworecki
(74) *Attorney, Agent, or Firm* — Studebaker & Brackett PC

(57) ABSTRACT

A radiation detector including: a substrate formed with a plural pixels in pixel region of a flexible base member, the plural pixels accumulates charges generated in response to light converted from radiation; a conversion layer provided at a surface to which the pixel region is provided on the base member, the conversion layer converts the radiation into light; and a reinforcement substrate provided at a surface of the conversion layer that faces a surface of the substrate side, the reinforcement substrate contains a material having a yield point and has a higher rigidity than the base member.

20 Claims, 53 Drawing Sheets

(30) Foreign Application Priority Data

| Nov. 22, 2018 | (JP) | JP2018-219696 |
| Feb. 8, 2019 | (JP) | JP2019-022148 |
| Feb. 8, 2019 | (JP) | JP2019-022149 |

(51) Int. Cl.
  *G01T 7/00* (2006.01)
  *A61B 6/00* (2006.01)
  *G01T 1/202* (2006.01)

(52) U.S. Cl.
  CPC ........ *G01T 1/2023* (2013.01); *G01T 1/20181* (2020.05); *G01T 7/00* (2013.01); *H01L 27/14661* (2013.01)

(56) References Cited

U.S. PATENT DOCUMENTS

| 2012/0211669 | A1* | 8/2012 | Itaya ........................ G01T 1/202 |
| | | | 264/1.37 |
| 2012/0217407 | A1 | 8/2012 | Iwakiri et al. |
| 2012/0256091 | A1 | 10/2012 | Nakahashi |
| 2012/0294425 | A1* | 11/2012 | Nagata ................ C23C 14/0694 |
| | | | 378/70 |
| 2013/0048864 | A1 | 2/2013 | Nakatsugawa |
| 2013/0140464 | A1 | 6/2013 | Iwakiri et al. |
| 2013/0154039 | A1 | 6/2013 | Furui et al. |
| 2015/0369931 | A1 | 12/2015 | Nakahashi |
| 2016/0183895 | A1 | 6/2016 | Harding |

FOREIGN PATENT DOCUMENTS

| JP | 2012-045370 A | 3/2012 |
| JP | 2012-128091 A | 7/2012 |
| JP | 2012-177624 A | 9/2012 |
| JP | 2012-189487 A | 10/2012 |
| JP | 2012-220659 A | 11/2012 |
| JP | 2013-050364 A | 3/2013 |
| JP | 2016-533642 A | 10/2016 |

OTHER PUBLICATIONS

International Preliminary Report on Patentability and Written Opinion issued in PCT/JP2019/009428; dated Sep. 22, 2020.

Office Action issued in JP 2020-508197; mailed by the Japanese Patent Office dated Nov. 17, 2020.

An Office Action issued by Taiwan Intellectual Property Office dated Aug. 1, 2022, which corresponds to Taiwanese Patent Application No. 108108695 and is related to U.S. Appl. No. 17/025,621; with partial English language translation.

The extended European search report issued by the European Patent Office dated Mar. 31, 2021, which corresponds to European Patent Application No. 19770823.3-1001 and is related to U.S. Appl. No. 17/025,621.

An Office Action issued by Taiwan Intellectual Property Office dated Sep. 27, 2022, which corresponds to Taiwanese Patent Application No. 108108695 and is related to U.S. Appl. No. 17/025,621; with partial English language translation.

Communication pursuant to Article 94(3) EPC issued by the European Patent Office dated Nov. 4, 2022, which corresponds to European Patent Application No. 19770823.3-1001 and is related to U.S. Appl. No. 17/025,621.

* cited by examiner

RADIATION DETECTOR, RADIOGRAPHIC IMAGING DEVICE, AND MANUFACTURING METHOD

CROSS-REFERENCE TO RELATED APPLICATIONS

This application is a continuation application of International Application No. PCT/JP2019/009428, filed on Mar. 8, 2019, which is incorporated herein by reference in its entirety. Further, this application claims priority from Japanese Patent Application No. 2018-051690, filed on Mar. 19, 2018, Japanese Patent Application No. 2018-182730, filed on Sep. 27, 2018, Japanese Patent Application No. 2018-219696, filed on Nov. 22, 2018, Japanese Patent Application No. 2019-022148, filed on Feb. 8, 2019, and Japanese Patent Application No. 2019-022149, filed on Feb. 8, 2019, the disclosure of which are incorporated by reference herein.

BACKGROUND

Technical Field

The present disclosure relates to a radiation detector, a radiographic imaging device, and a manufacturing method.

Related Art

Radiographic imaging devices that perform radiographic imaging for medical diagnostic purposes are known. In such radiographic imaging devices, a radiation detector is employed to generate radiographic images by detecting radiation that has passed through an imaging subject (see, for example, Japanese Patent Application Laid-Open (JP-A) Nos. 2009-133837 and 2012-177624).

Such radiation detectors may include a conversion layer such as a scintillator to convert radiation into light, and a substrate including a pixel region on a base member, the pixel region being provided with plural pixels that accumulate charges generated in response to light converted by the conversion layer. The use of a flexible base member as the base member of the substrate of such a radiation detector is known. Employing a flexible base member may for example enable a reduction in weight of the radiographic imaging device (radiation detector) or facilitate imaging of the imaging subject.

However, the radiation detector may be handled on its own during processes to manufacture the radiographic imaging device and the like. When handling the radiation detector on its own, there is a concern that the conversion layer might detach from the substrate, for example due to the effects of bending of the flexible substrate.

In the technology described in JP-A No. 2009-133837, a conversion layer is provided with an electromagnetic shielding layer that covers an opposite-side surface of the conversion layer to a surface on a substrate side. In the technology described in JP-A No. 2012-177624, a support body that supports a conversion layer is provided on an opposite-side surface of the conversion layer to a surface on a substrate side. However, the technology described in JP-A Nos. 2009-133837 and 2012-177624 do not consider cases in which a radiation detector is handled on its own. Accordingly, the electromagnetic shielding layer of JP-A No. 2009-133837 and the support body of JP-A No. 2012-177624 may not be able to suppress detachment of the conversion layer from the substrate when the radiation detector is handled on its own.

SUMMARY

The present disclosure provides a radiation detector, a radiographic imaging device, and a manufacturing method that are better capable of suppressing breakage of a conversion layer when a radiation detector is on its own than in cases in which consideration is not given to the material of a reinforcement substrate provided to an opposite-side surface of a conversion layer to a surface on a substrate side.

A first aspect of the present disclosure is a radiation detector including: a substrate formed with plural pixels in a pixel region of a flexible base member, the plural pixels accumulates charges generated in response to light converted from radiation; a conversion layer provided at a surface to which the pixel region is provided on the base member, the conversion layer converts the radiation into light; and a reinforcement substrate provided at a surface of the conversion layer that faces a surface of the substrate side, the reinforcement substrate contains a material having a yield point and has a higher rigidity than the base member.

A radiation detector of a second aspect of the present disclosure is the radiation detector of the first aspect, wherein the reinforcement substrate is provided at a region that is wider than a region provided with the conversion layer.

A radiation detector of a third aspect of the present disclosure is the radiation detector of the first aspect or the radiation detector of the second aspect, wherein: the substrate includes a connection region in a region at an outer periphery of a surface to which the plural pixels are formed, the connection region being connected with another end of flexible wiring which is connected with a circuit section for reading the charges accumulated in the plural pixels; and the reinforcement substrate is provided in a region covering the conversion layer and at least a portion of the connection region.

A radiation detector of a fourth aspect of the present disclosure is the radiation detector of any one of the first aspect to the third aspect, further including a reinforcement member at a surface of the substrate that faces a surface to which the plural pixels are formed, the reinforcement member having a higher rigidity than the base member.

A radiation detector of a fifth aspect of the present disclosure is the radiation detector of any one of the first aspect to the fourth aspect, further including a buffer layer provided between the substrate and the conversion layer.

A radiation detector of a sixth aspect of the present disclosure is the radiation detector of any one of the first aspect to the fifth aspect, wherein the reinforcement substrate has a bending elastic modulus of from 1000 MPa to 2500 MPa.

A radiation detector of a seventh aspect of the present disclosure is the radiation detector of any one of the first aspect to the sixth aspect, wherein the material having a yield point is at least one material out of polycarbonate or polyethylene terephthalate.

A radiation detector of an eighth aspect of the present disclosure is the radiation detector of any one of the first aspect to the seventh aspect, wherein a ratio of a coefficient of thermal expansion of the reinforcement substrate with respect to a coefficient of thermal expansion of the conversion layer is from 0.5 to 2.

A radiation detector of a ninth aspect of the present disclosure is the radiation detector of any one of the first aspect to the eighth aspect, wherein the reinforcement substrate has a coefficient of thermal expansion of from 30 ppm/K to 80 ppm/K.

A radiation detector of a tenth aspect of the present disclosure is the radiation detector of any one of the first aspect to the ninth aspect, wherein the conversion layer includes columnar crystals of CsI.

A radiation detector of an eleventh aspect of the present disclosure is the radiation detector of any one of the first aspect to the tenth aspect, wherein the plural pixels are formed in the pixel region by a direct formation method.

A radiographic imaging device of a twelfth aspect of the present disclosure includes: the radiation detector of any one of the first aspect to the eleventh aspect; a control section that outputs a control signal for reading the charges accumulated in the plural pixels; and a circuit section electrically connected to the radiation detector by flexible wiring, circuit section reads out charges from the plural pixels in response to the control signal.

A thirteenth aspect of the present disclosure is a manufacturing method for a radiation detector, including: a process of coating an adhesion layer onto a reinforcement substrate having a size according to the size of a radiation detector; a process of forming a substrate by providing a flexible base member to a support body with a separation layer interposed between the base member and the support body, and providing a plural pixels in a pixel region of the base member, the plural pixels accumulates charges generated in response to light converted from radiation; a process of forming a conversion layer that converts the radiation into light at a surface to which the pixel region of the base member is provided; a process of affixing a reinforcement substrate at a surface of the conversion layer opposite to a surface that faces a surface of the substrate side, the reinforcement substrate containing a material having a yield point and having a higher rigidity than the base member; and a process of separating the substrate provided with the conversion layer and the reinforcement substrate from the support body.

A manufacturing method of a fourteenth aspect of the present disclosure is the manufacturing method of the thirteenth aspect, further including, prior to the process of affixing the reinforcement substrate, a process of connecting one end of flexible wiring, which is connected to a circuit section that reads out the charges accumulated in the plural pixels, to the substrate.

The present disclosure may better suppress breakage of the conversion layer when the radiation detector is on its own, than in cases in which consideration is not given to the material of the reinforcement substrate provided to the opposite-side surface of the conversion layer to the surface on the substrate side.

DESCRIPTION OF EMBODIMENTS

Detailed explanation follows regarding exemplary embodiments of the present invention, with reference to the drawings. Note that the present invention is not limited by these exemplary embodiments.

First Exemplary Embodiment

A radiation detector of the present exemplary embodiment has a function of outputting image information expressing radiographic images of an imaging subject by detecting radiation that has passed through the imaging subject. The radiation detector of the present exemplary embodiment includes a thin film transistor (TFT) substrate and a conversion layer configured to convert radiation into light (a TFT substrate 12 and a conversion layer 14 of a radiation detector 10, see FIG. 4).

Figure 1:
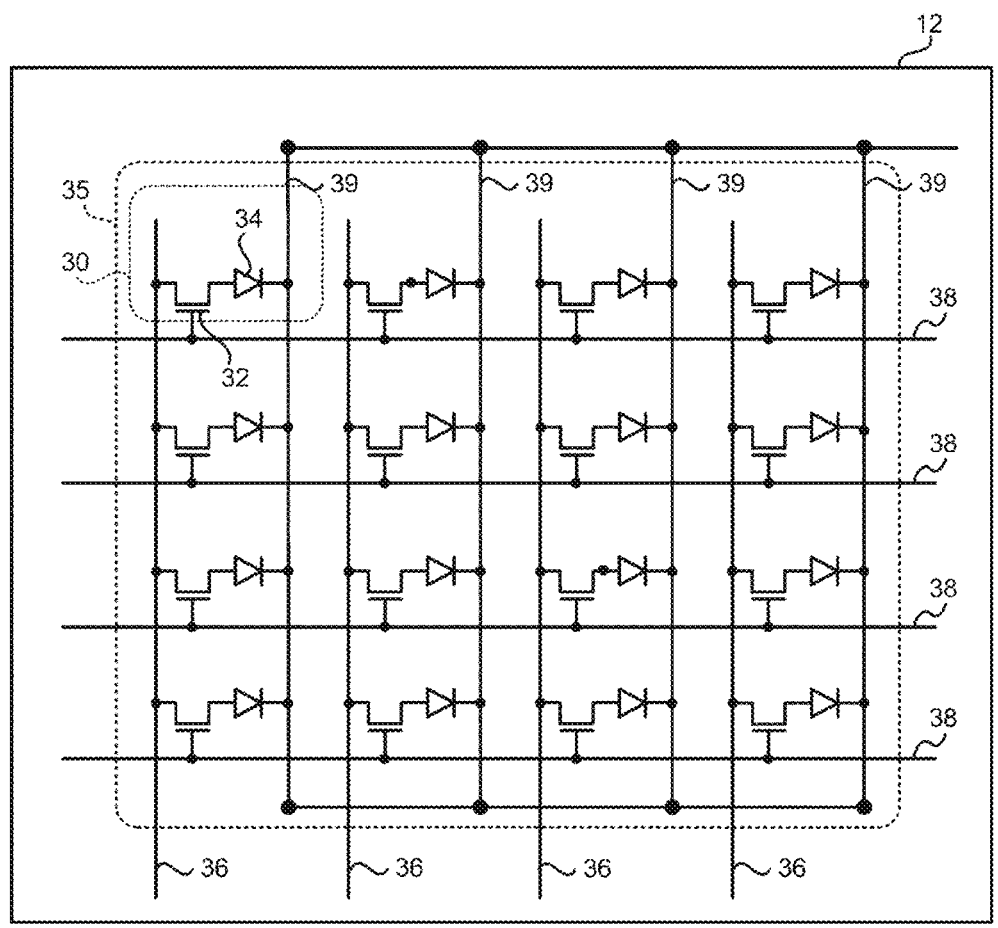
FIG. 1 is a diagram illustrating an example of configuration a thin film transistor (TFT) substrate of a radiation detector of a first exemplary embodiment.

First, explanation follows regarding an example of configuration of the TFT substrate 12 of the radiation detector of the present exemplary embodiment, with reference to FIG. 1. Note that the TFT substrate 12 of the present exemplary embodiment is a substrate in which a pixel array 31 including plural pixels 30 is formed in a pixel region 35 of a base member 11. Accordingly, the expression "pixel region 35" is synonymous with the "pixel array 31". The TFT substrate 12 of the present exemplary embodiment is an example of a substrate of technology disclosed herein.

The base member 11 is made of resin, and is flexible. For example, the base member 11 is a resin sheet including a plastic such as polyimide. The thickness of the base member 11 may be any thickness that enables the desired flexibility to be obtained, set according to the hardness of the material, the size of the TFT substrate 12, and the like. For example, in cases in which the base member 11 is configured by a resin sheet, the base member 11 should have a thickness of from 5 μm to 125 μm, and more preferably has a thickness of from 20 μm to 50 μm.

Note that the base member 11 has characteristics capable of withstanding manufacture of the pixels 30, as will be described in detail later, and in the present exemplary embodiment, has characteristics capable of withstanding the manufacture of amorphous silicon TFTs (a-Si TFTs). Preferable characteristics of the base member 11 are a coefficient of thermal expansion in a range of from 300° C. to 400° C. that is similar to that of an silicon (Si) wafer (for example ±5 ppm/K), and more specifically preferably no greater than 20 ppm/K. The heat shrinkage ratio of the base member 11 in a machine direction (MD) at 400° C. and at a thickness of 25 μm is preferably a heat shrinkage ratio of no greater than 0.5%. Moreover, the modulus of elasticity of the base member 11 preferably does not have a transition point in a temperature region of from 300° C. to 400° C., as is typical of an ordinary polyimide, and preferably has a modulus of elasticity at 500° C. of no less than 1 GPa.

Figure 2:
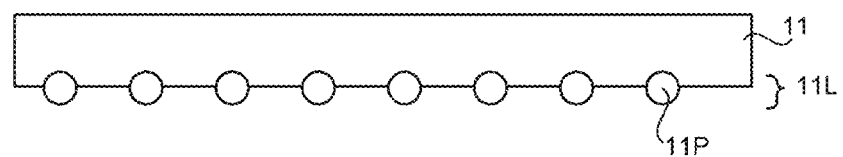
FIG. 2 is a cross-section to explain an example of a base member of an exemplary embodiment.

Moreover, as illustrated in FIG. 2, the base member 11 of the present exemplary embodiment preferably includes a fine particle layer 11L containing inorganic fine particles 11P having a mean particle size of from 0.05 μm to 2.5 μm on an opposite-side surface to the side provided with the conversion layer 14. XENOMAX (registered trademark) is a specific example of a resin sheet having such characteristics.

Note that the thickness discussed in the present exemplary embodiment is measured using a micrometer. The coefficient of thermal expansion is measured according to JIS K7197:1991. In this measurement, test pieces are cut from a main face of the base member 11 while changing the angle thereof by 15 degrees each time, the coefficient of thermal expansion is measured for each of the cut test pieces, and the highest value obtained is taken to be the coefficient of thermal expansion of the base member 11. The measurements of the coefficient of thermal expansion in the machine direction (MD) and a transverse direction (TD) are performed at 10° C. intervals over a range of from −50° C. to 450° C. with ppm/° C. converted into ppm/K. A TMA4000S instrument made by MAC Science Co., Ltd. is employed to measure the coefficient of thermal expansion using a sample length of 10 mm, a sample width of 2 mm, an initial load of 34.5 g/mm$^2$, a rate of temperature increase of 5° C./min, and an argon atmosphere. The modulus of elasticity is measured according to JIS K7171:2016. Note that in this measurement, test pieces are cut from a main face of the base member 11 while changing the angle thereof by 15 degrees each time, a stretch test is performed on each of the cut test pieces, and the highest value obtained is taken to be the modulus of elasticity of the base member 11.

Each of the pixels 30 includes a sensor section 34 that accumulates an charges generated in response to light converted by the conversion layer, and a switching element 32 that reads the accumulated charges from the sensor section 34. As an example, in the present exemplary embodiment, a thin film transistor (TFT) is employed as the switching element 32. The switching element 32 is thus referred to as the "TFT 32" hereafter.

The plural pixels 30 are arranged along one direction (a scan line direction corresponding to the lateral direction in FIG. 1, hereafter also referred to as the "row direction") and along a direction intersecting the row direction (a signal line direction corresponding to the longitudinal direction in FIG. 1, hereafter also referred to as the "column direction") to form a two-dimensional pattern in the pixel region 35 of the TFT substrate 12. Although the array of the pixels 30 is simplified in the illustration of FIG. 1, for example 1024× 1024 of the pixels 30 are arranged along the row direction and the column direction.

The radiation detector 10 is further provided with plural scan lines 38 to control switching states (ON and OFF states) of the TFTs 32, and plural signal lines 36 that intersect the plural scan lines 38 and correspond to each column of the pixels 30 to read the accumulated charges from the sensor sections 34. Each of the plural scan lines 38 is connected to a drive section 103 (see FIG. 5) provided externally to the radiation detector 10 through a connection region 43 (see FIG. 4 and FIG. 5) provided on the TFT substrate 12, so as to allow a flow of control signals output from the drive section 103 to control the switching states of the TFTs 32. Moreover, each of the plural signal lines 36 is connected to a signal processing section 104 (see FIG. 5) provided externally to the radiation detector 10 through a connection region 43 (see FIG. 4 and FIG. 5) provided on the TFT substrate 12, such that charges read from the pixels 30 are output to the signal processing section 104.

Common lines 39 are provided along the wiring direction of the signal lines 36 to the sensor sections 34 of the corresponding pixels 30 in order to apply a bias voltage to the corresponding pixels 30. Each of the common lines 39 is connected to a bias power source external to the radiation detector 10 through a pad (not illustrated in the drawings) provided on the TFT substrate 12, such that the bias voltage from the bias power source is applied to the corresponding pixels 30.

Figure 3:
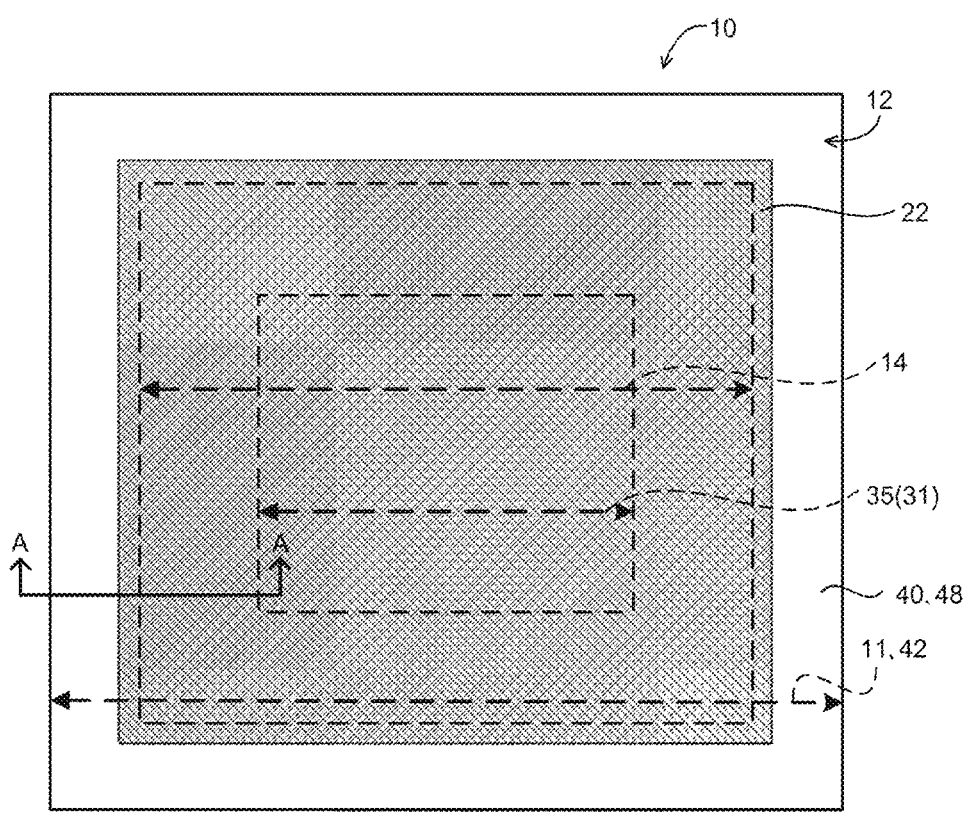
FIG. 3 is a plan view illustrating an example of a radiation detector of the first exemplary embodiment, as viewed from a side provided with a conversion layer.
Figure 4:
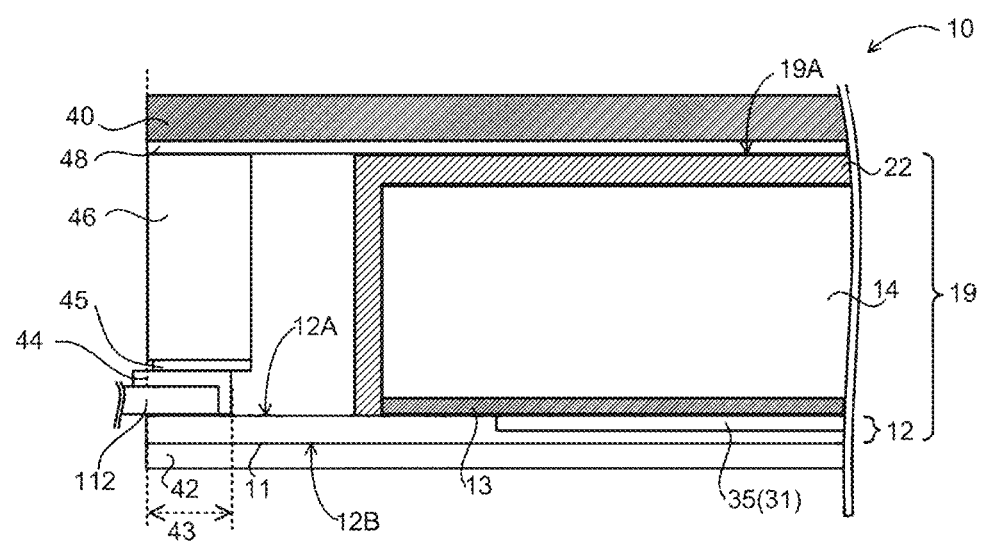
FIG. 4 is a cross-section of the radiation detector illustrated in FIG. 3 as sectioned along line A-A.

In the radiation detector 10 of the present exemplary embodiment, the conversion layer is formed on the TFT substrate 12. FIG. 3 is a plan view illustrating the radiation detector 10 of the present exemplary embodiment as viewed from a side formed with the conversion layer 14. FIG. 4 is a cross-section of the radiation detector 10 illustrated in FIG. 3, as sectioned along line A-A. In the following explanation, reference to "on top" with respect to the structure of the radiation detector 10 refers being on top in a positional relationship referenced against the TFT substrate 12 side. For example, the conversion layer 14 is provided on top of the TFT substrate 12.

As illustrated in FIG. 3 and FIG. 4, the conversion layer 14 of the present exemplary embodiment is provided on top of a region configuring a portion of a first surface 12A of the TFT substrate 12 that includes the pixel region 35. Thus, the conversion layer 14 of the present exemplary embodiment is not provided on top of a region corresponding to an outer peripheral portion of the first surface 12A of the TFT substrate 12. The first surface 12A of the present exemplary embodiment is an example of a pixel region-provided surface of the present disclosure.

In the present exemplary embodiment, a scintillator containing cesium iodide (CsI) is employed as an example of the conversion layer 14. For example, the scintillator preferably contains thallium-doped cesium iodide (CsI:Tl) or sodium-doped cesium iodide (CsI:Na) that has light emission spectra of from 400 nm to 700 nm when irradiated with X-rays. Note that the peak light emission wavelength of CsI:Tl in the visible light region is 565 nm.

In the radiation detector 10 of the present exemplary embodiment, the conversion layer 14 is formed from strip shaped columnar crystals (not illustrated in the drawings) formed directly on top of the TFT substrate 12 using a vapor phase deposition method such as a vacuum deposition method, a sputtering method, or a chemical vapor deposition (CVD) method. As an example of the formation method of the conversion layer 14, in cases in which CsI:Tl is used as the conversion layer 14, a vacuum deposition method may be applied in which the CsI:Tl is heated and vaporized, for example using a resistance heating crucible under environmental conditions of a vacuum of from 0.01 Pa to 10 Pa, and the CsI:Tl is deposited on top of the TFT substrate 12 with the TFT substrate 12 at a temperature between room temperature (20° C.) and 300° C. The thickness of the conversion layer 14 is preferably from 100 μm to 800 μm.

In the present exemplary embodiment, as illustrated in FIG. 4 as an example, a buffer layer 13 is provided between the TFT substrate 12 and the conversion layer 14. The buffer layer 13 has a function of buffering a difference between the coefficient of thermal expansion of the conversion layer 14 and the coefficient of thermal expansion of the base member 11. Note that although a configuration differing from that of the radiation detector 10 of the exemplary embodiment of the present disclosure may be made in which the buffer layer 13 is not provided, providing the buffer layer 13 is more preferable the greater the difference between the coefficient of thermal expansion of the conversion layer 14 and the coefficient of thermal expansion of the base member 11. For example, in cases in which XENOMAX (registered trademark) is employed for the base member 11, the difference to the coefficient of thermal expansion of the conversion layer 14 is greater than it would be with other materials, and so the buffer layer 13 is preferably provided as in the radiation detector 10 illustrated in FIG. 4. A polyimide (PI) film or a Parylene (registered trademark) film may be employed as the buffer layer 13.

A protective layer 22 has a function of protecting the conversion layer 14 from moisture such as humidity. Examples of materials that may be employed as the material of the protective layer 22 include organic films such as single layer films or stacked films of polyethylene terephthalate (PET), polyphenylene sulfide (PPS), oriented polypropylene (OPP), PEN (polyethylene naphthalate), PI, and the like. Moreover, an ALPET (registered trademark) sheet in which aluminum, for example a bonded aluminum foil, is stacked on an insulating sheet (film) such as PET may be employed as the protective layer 22.

A stacked body 19 configured by stacking the TFT substrate 12, the buffer layer 13, the conversion layer 14, and the protective layer 22 includes a first surface 19A, this being a surface on the side of the conversion layer 14. A reinforcement substrate 40 is provided on the first surface 19A using an adhesion layer 48 or the like.

The reinforcement substrate 40 has a higher rigidity than the base member 11, such that dimensional change (deformation) with respect to force applied in a direction perpendicular to a surface opposing the conversion layer 14 is smaller than the dimensional change with respect to force applied in a direction perpendicular to the first surface 12A of the TFT substrate 12. The thickness of the reinforcement substrate 40 of the present exemplary embodiment is also greater than the thickness of the base member 11. Note that the rigidity referred to here refers to the difficulty of bending the reinforcement substrate 40 and the base member 11, encompassing the thicknesses of the reinforcement substrate 40 and the base member 11, with bending becoming more difficult the greater the rigidity.

The reinforcement substrate 40 of the present exemplary embodiment is a substrate containing a material having a yield point. In the present exemplary embodiment, the "yield point" refers to the point at which yielding occurs on a curve expressing the relationship between stress and strain in the phenomenon in which stress suddenly decreases when the material is applied with tension. Examples of resins having a yield point are generally hard resins with high viscosity, and soft resins with high viscosity and moderate strength. At least one out of polycarbonate (PC) or polyamide is an example of a hard resin with high viscosity. At least one out of high density polyethylene or polypropylene is an example of a soft resin with high toughness and moderate strength.

The reinforcement substrate 40 of the present exemplary embodiment preferably has a bending elastic modulus of from 1000 MPa to 2500 MPa. The bending elastic modulus is, for example, measured according to the method set out in JIS K7171:2016. If the bending elastic modulus is lower than this, the thickness of the reinforcement substrate 40 has to be increased to obtain rigidity. From the perspective of suppressing the thickness, the bending elastic modulus of the reinforcement substrate 40 is more preferably from 2000 MPa to 2500 MPa.

The coefficient of thermal expansion (CTE) of the reinforcement substrate 40 of the present exemplary embodiment is preferably close to the coefficient of thermal expansion of the material of the conversion layer 14, and more preferably the ratio of the coefficient of thermal expansion of the reinforcement substrate 40 with respect to the coefficient of thermal expansion of the conversion layer 14 is from 0.5 to 2. For example, in cases in which CsI:Tl is employed as the material of the conversion layer 14, the coefficient of thermal expansion thereof is 50 ppm/K. In such cases, examples of materials that may be employed for the reinforcement substrate 40 include polyvinyl chloride (PVC) with a coefficient of thermal expansion of from 60 ppm/K to 80 ppm/K, acrylic with a coefficient of thermal expansion of from 70 ppm/K to 80 ppm/K, PET with a coefficient of thermal expansion of from 65 ppm/K to 70 ppm/K, PC with a coefficient of thermal expansion of 65 ppm/K, and TEFLON (registered trademark) with a coefficient of thermal expansion of from 45 ppm/K to 70 ppm/K. In consideration of the bending elastic modulus described above, the material of the reinforcement substrate 40 is more preferably a material containing at least one out of PET or PC.

As illustrated in FIG. 3 and FIG. 4, the reinforcement substrate 40 of the present exemplary embodiment is provided over a wider region of the first surface 12A of the TFT substrate 12 than a region provided with the conversion layer 14. As illustrated in FIG. 3 and FIG. 4, an end portion of the reinforcement substrate 40 projects out further toward an outer side (an outer peripheral portion side of the TFT substrate 12) than an outer peripheral portion of the conversion layer 14.

Figure 5:
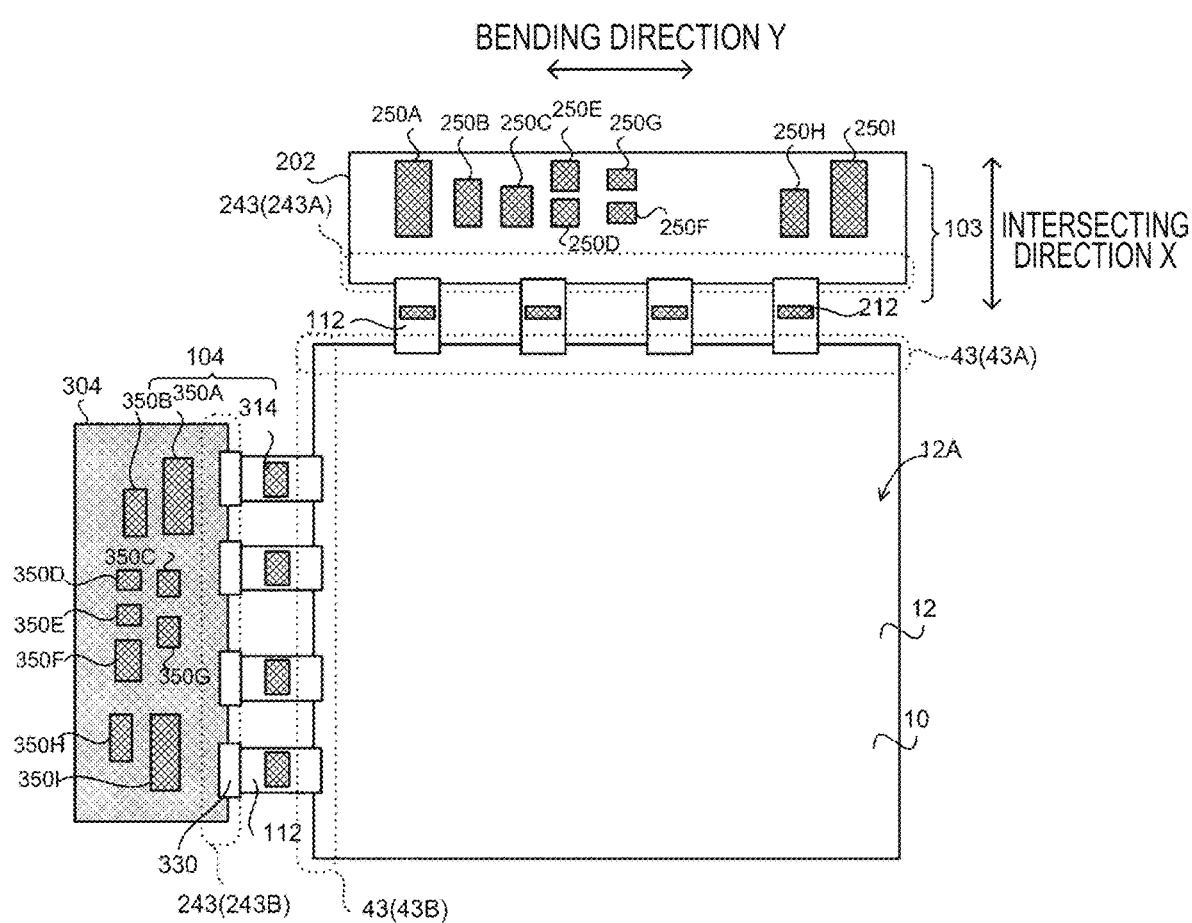
FIG. 5 is a plan view illustrating an example of a radiation detector of the first exemplary embodiment, as viewed from the side of a first surface of a TFT substrate.

As illustrated in FIG. 4, the connection regions 43 are provided in the outer peripheral portion of the TFT substrate 12. Flexible cables 112, described in detail later, are connected to the connection regions 43. The flexible cables 112 are connected to at least one out of the drive section 103 or the signal processing section 104 (see FIG. 5 for both). The drive section 103 and the signal processing section 104 of the present exemplary embodiment are examples of circuit sections of the present disclosure. FIG. 5 is a plan view illustrating an example of a state in which the drive section 103 and the signal processing section 104 are connected to the radiation detector 10 of the present exemplary embodiment, as viewed from the first surface 12A side of the TFT substrate 12.

As illustrated in the example of FIG. 5, the flexible cables 112 are electrically connected to the connection regions 43 of the TFT substrate 12. Note that in the present exemplary embodiment, unless specifically stated otherwise, "connection" in the context of components including the flexible cables 112 that are described as "cables" refers to an electrical connection. Note that the flexible cables 112 include conductive signal lines (not illustrated in the drawings), such signal lines being electrically connected by being connected to the connection regions 43. The flexible cables 112 of the present exemplary embodiment are an example of flexible wiring of the present disclosure. Hereafter, "cables" are understood to be flexible (have flexibility).

One ends of plural of the flexible cables 112 (four in FIG. 5) are thermally compressed onto the corresponding connection region 43 (43A) of the TFT substrate 12. These flexible cables 112 have a function of connecting the drive section 103 and the scan lines 38 (see FIG. 1) together. The plural signal lines (not illustrated in the drawings) included in the flexible cables 112 are connected to the scan lines 38 (see FIG. 1) of the TFT substrate 12 through the connection region 43.

The other ends of the flexible cables 112 are thermally compressed onto a connection region 243 (243A) provided in a region at an outer periphery of a drive substrate 202. The plural signal lines (not illustrated in the drawings) included in the flexible cables 112 are connected to drive components 250, these being circuits, elements, and the like mounted on the drive substrate 202, through the connection region 243.

FIG. 5 illustrates an example of a state in which nine drive components 250 (250A to 250I) are mounted on the drive substrate 202. As illustrated in FIG. 5, the drive components 250 of the present exemplary embodiment are arranged along an intersecting direction X that intersects a bending direction Y, this being a direction along a side corresponding to the connection region 43 (43A) of the TFT substrate 12.

The drive substrate 202 of the present exemplary embodiment is a flexible printed circuit board (PCB), configuring what is referred to as a flexible substrate. The drive components 250 mounted on the drive substrate 202 are primarily components involved in digital signal processing (referred to hereafter as "digital system components"). Specific examples of the drive components 250 include digital buffers, bypass capacitors, pull-up and pull-down resistors, damping resistors, and electromagnetic compatibility (EMC) chip components. Note that the drive substrate 202 does not necessary have to be a flexible substrate, and may be a non-flexible, rigid substrate, as described later.

Digital system components tend to have a smaller surface area (size) than analog system components, described later. Moreover, digital system components tend to be less susceptible to being strongly affected by electrical interference, in other words noise, than analog system components. Accordingly, in the present exemplary embodiment, the drive substrate 202 mounted with the drive components 250 is configured on a side that bends accompanying bending of the TFT substrate 12 when the TFT substrate 12 bends.

Drive circuit sections 212 are also mounted on the flexible cables 112 connected to the drive substrate 202. The drive circuit sections 212 are connected to the plural signal lines (not illustrated in the drawings) included in the flexible cables 112.

In the present exemplary embodiment, the drive section 103 is implemented by the drive components 250 mounted on the drive substrate 202 and the drive circuit sections 212. The drive circuit sections 212 are integrated circuits (IC) that include different circuits to those of the drive components 250 mounted on the drive substrate 202 out of the various circuits and elements used to implement the drive section 103.

In this manner, in the radiation detector 10 of the present exemplary embodiment, the TFT substrate 12 and the drive substrate 202 are electrically connected by the flexible cables 112 in order to connect the drive section 103 and the scan lines 38 together.

One ends of plural of the flexible cables 112 (four in FIG. 5) are thermally compressed onto the corresponding connection region 43 (43B) of the TFT substrate 12. The plural signal lines (not illustrated in the drawings) included in these flexible cables 112 are connected to the signal lines 36 (see FIG. 1) through the connection region 43. The flexible cables 112 have a function of connecting the signal processing section 104 and the signal lines 36 (see FIG. 1) together.

The other ends of the flexible cables 112 are electrically connected to connectors 330 provided in a connection region 243 (243B) of a signal processing substrate 304. The plural signal lines (not illustrated in the drawings) included in the flexible cables 112 are connected to signal processing components 350, these being circuits, elements, and the like mounted on the signal processing substrate 304, through the connectors 330. Examples of the connectors 330 include connectors with zero insertion force (ZIF) structures, and connectors with non-ZIF structures. As an example, FIG. 5 illustrates a state in which nine of the signal processing components 350 (350A to 350I) are mounted on the signal processing substrate 304. As illustrated in FIG. 5, the signal processing components 350 of the present exemplary embodiment are disposed along the intersecting direction X, this being a direction running along the connection region 43 (43B) of the TFT substrate 12.

Note that the signal processing substrate 304 of the present exemplary embodiment is a non-flexible PCB substrate, namely what is referred to as a rigid substrate. Accordingly, the thickness of the signal processing substrate 304 is greater than the thickness of the drive substrate 202. The signal processing substrate 304 also has a higher rigidity than the drive substrate 202.

The signal processing components 350 mounted on the signal processing substrate 304 are primarily components employed in analog signal processing (referred to hereafter as analog system components). Specific examples of the signal processing components 350 include operational amplifiers, analog-digital converters (ADCs), digital-analog converters (DACs), and power source ICs. The signal processing components 350 of the present exemplary embodiment also include power source coils and high-capacity smoothing capacitors, these being comparatively large components.

As described above, the analog system components tend to have a larger surface area (size) than the digital system components. Furthermore, the analog system components tend to be more susceptible to the effects of electrical interference, in other words noise, than the digital system components. Accordingly, in the present exemplary embodiment, the signal processing substrate 304 mounted with the signal processing components 350 is configured on a side of the substrate that does not bend (is not affected by bending) when the TFT substrate 12 bends.

Signal processing circuit sections 314 are mounted on the flexible cables 112 connected to the signal processing substrate 304. The signal processing circuit sections 314 are connected to the plural signal lines (not illustrated in the drawings) included in the flexible cables 112.

In the present exemplary embodiment, the signal processing section 104 is implemented by the signal processing components 350 mounted on the signal processing substrate 304 and by the signal processing circuit sections 314. Out of the various circuits and elements used to implement the signal processing section 104, the signal processing circuit sections 314 are ICs including different circuits to the signal processing components 350 mounted on the signal processing substrate 304.

In this manner, in the radiation detector 10 of the present exemplary embodiment, the TFT substrate 12 and the signal processing substrate 304 are electrically connected by the flexible cables 112 so as to connect the signal processing section 104 and the respective signal lines 36 together.

As in the example illustrated in FIG. 4, the radiation detector 10 of the present exemplary embodiment further includes a spacer 46 provided between the reinforcement substrate 40 and the first surface 12A of the TFT substrate 12 so as to seal a side face of the conversion layer 14. The flexible cables 112, an anti-moisture agent 44, and an adhesion layer 45 are sandwiched between the spacer 46 and the TFT substrate 12.

The method of providing the spacer 46 is not particularly limited, and for example the spacer 46 may be affixed to the adhesion layer 48 at an end portion of the reinforcement substrate 40, and the reinforcement substrate 40 may then be affixed to the TFT substrate 12 in a state in which the spacer 46 has been provided to the reinforcement substrate 40 and in a state in which the stacked body 19, the flexible cables 112, the anti-moisture agent 44, and the adhesion layer 45 have been provided to the TFT substrate 12, such that the spacer 46 is thus provided between the TFT substrate 12 and the reinforcement substrate 40. Note that the width of the spacer 46 (in a direction intersecting the stacking direction of the stacked body 19) is not limited to the example illustrated in FIG. 4. For example, the width of the spacer 46 may be increased to a position closer to the conversion layer 14 than that illustrated in the example of FIG. 4. Alternatively, the spacer 46 may be formed by caulking with resin, ceramic, or the like on the first surface 12A of the TFT substrate 12.

A protective film 42 that has a function of protecting from moisture such as humidity is provided on a second surface 12B of the TFT substrate 12 of the present exemplary embodiment. Materials configuring the protective film 42 may, for example, be the same as the materials employed for the protective layer 22.

Explanation follows regarding an example of a manufacturing method of the radiation detector 10 of the present exemplary embodiment. The example of a manufacturing method of the radiation detector 10 of the present exemplary embodiment is explained with reference to FIG. 6 and FIG. 7.

The reinforcement substrate 40 is pre-prepared in a desired size appropriate for the radiation detector 10, in a state coated with the adhesion layer 48 and provided with the spacer 46 on the adhesion layer 48.

Figure 6:
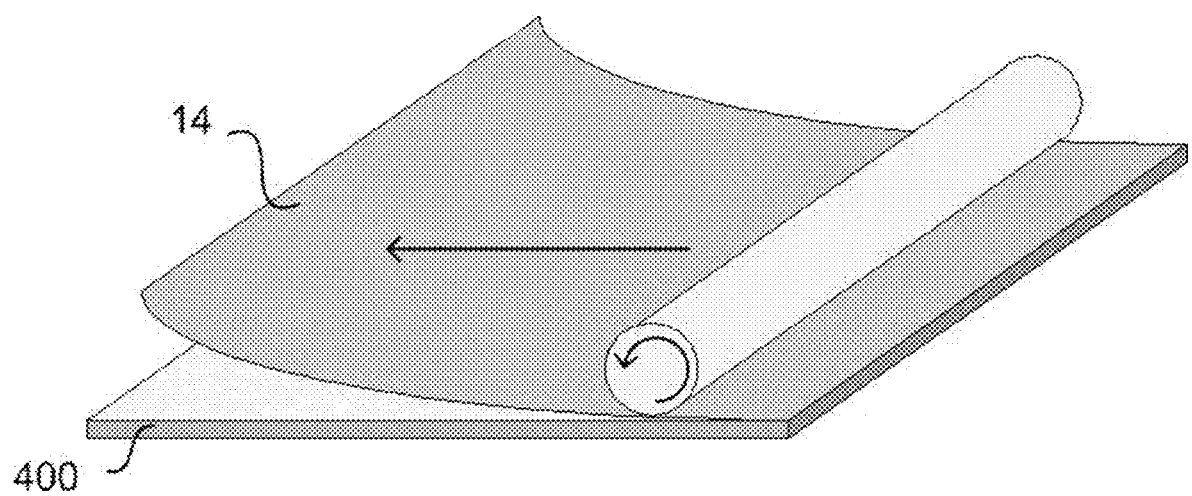
FIG. 6 is an explanatory diagram to explain an example of a manufacturing method of a radiation detector of the first exemplary embodiment.

As illustrated in FIG. 6, the base member 11 is formed on a support body 400 such as a glass substrate with a greater thickness than the base member 11 with a separation layer (not illustrated in the drawings) interposed therebetween. In cases in which the base member 11 is formed by a lamination method, a sheet configuring the base member 11 is affixed onto the support body 400. A surface corresponding to the second surface 12B of the TFT substrate 12 of the base member 11 contacts the separation layer (not illustrated in the drawings).

The plural pixels 30 are then formed in the pixel region 35 of the base member 11. Note that as an example, in the present exemplary embodiment, the plural pixels 30 are formed in the pixel region 35 of the base member 11 with an undercoat layer (not illustrated in the drawings) employing SiN or the like interposed therebetween.

The conversion layer 14 is then formed on top of the pixel region 35. In the present exemplary embodiment, first the buffer layer 13 is formed in a region of the first surface 12A of the TFT substrate 12 to be provided with the conversion layer 14. Then, the conversion layer 14 is formed on top of the TFT substrate 12, and more specifically directly on top of the buffer layer 13, by columnar crystals of CsI directly formed using a vapor phase deposition method such as a vacuum deposition method, a sputtering method, or a chemical vapor deposition (CVD) method. When this is performed, the side of the conversion layer 14 contacting the pixels 30 corresponds to the start side in the growth direction of the columnar crystals.

Note that in cases in which the CsI conversion layer 14 is directly provided on top of the TFT substrate 12 using a vapor phase deposition method in this manner, the opposite-side surface of the conversion layer 14 to the side contacting the TFT substrate 12 may, for example, be provided with a reflective layer (not illustrated in the drawings) having a function of reflecting light converted by the conversion layer 14. Such a reflective layer may be directly provided to the conversion layer 14, or may be provided with a cohesion layer or the like interposed therebetween. An organic material is preferably employed as the material of the reflective layer, and for example a material employing at least one material out of white PET, $TiO_2$, $Al_2O_3$, foamed white PET, a highly reflective polyester sheet, or a specular reflective aluminum is preferably employed. In particular, from the perspective of reflectivity, a white PET material is preferably employed. Note that a highly reflective polyester sheet is a sheet (film) having a multi-layered structure of plural overlapping thin polyester sheets.

In cases in which a CsI scintillator is employed as the conversion layer 14, the conversion layer 14 may be formed on the TFT substrate 12 using a different method to that of the present exemplary embodiment. For example, vapor deposition of CsI on an aluminum sheet or the like may be performed using a vapor phase deposition method, and the conversion layer 14 may be formed on the TFT substrate 12 by affixing the side of the CsI that does not contact the aluminum sheet and the pixels 30 of the TFT substrate 12 together using an adhesive sheet or the like. In such cases, a product obtained by covering the overall conversion layer 14 including the aluminum sheet with a protective film is preferably affixed to the pixel region 35 of the TFT substrate 12. Note that in such cases, the side of the conversion layer 14 contacting the pixel region 35 configures a growth direction tip end side of the columnar crystals.

Unlike the radiation detector 10 of the present exemplary embodiment, GOS ($Gd_2O_2S$:Tb) or the like may be employed in place of CsI as the conversion layer 14. In such cases, a sheet on which GOS has been distributed using a resin binder or the like may be affixed to a support body formed from white PET or the like using an adhesion layer or the like, and the side of the GOS that is not affixed to the support body may be affixed to the pixel region 35 of the TFT substrate 12 using an adhesive sheet or the like to form the conversion layer 14 on the TFT substrate 12. Note that the efficiency of radiation to visible light conversion is greater when CsI is employed than when GOS is employed for the conversion layer 14.

The flexible cables 112 are then thermally compressed onto the connection regions 43 (43A and 43B) of the TFT substrate 12, to electrically connect the plural signal lines (not illustrated in the drawings) included in the flexible cables 112 to the connection regions 43 (43A and 43B) of the TFT substrate 12.

The flexible cables 112 are then thermally compressed onto the connection region 243 (243A) of the drive substrate 202 to electrically connect the plural signal lines (not illustrated in the drawings) included in the flexible cables 112 to the drive components 250 mounted on the drive substrate 202.

The pre-prepared reinforcement substrate 40 provided with the spacer 46 is then affixed to the TFT substrate 12 on which the conversion layer 14 has been formed and to which the flexible cables 112 have been connected, thus sealing the conversion layer 14. Note that this affixing may be performed under atmospheric pressure or under a reduced pressure (in a vacuum). Reduced pressure is preferable in order to suppress air and the like from being incorporated between affixed components.

Figure 7:
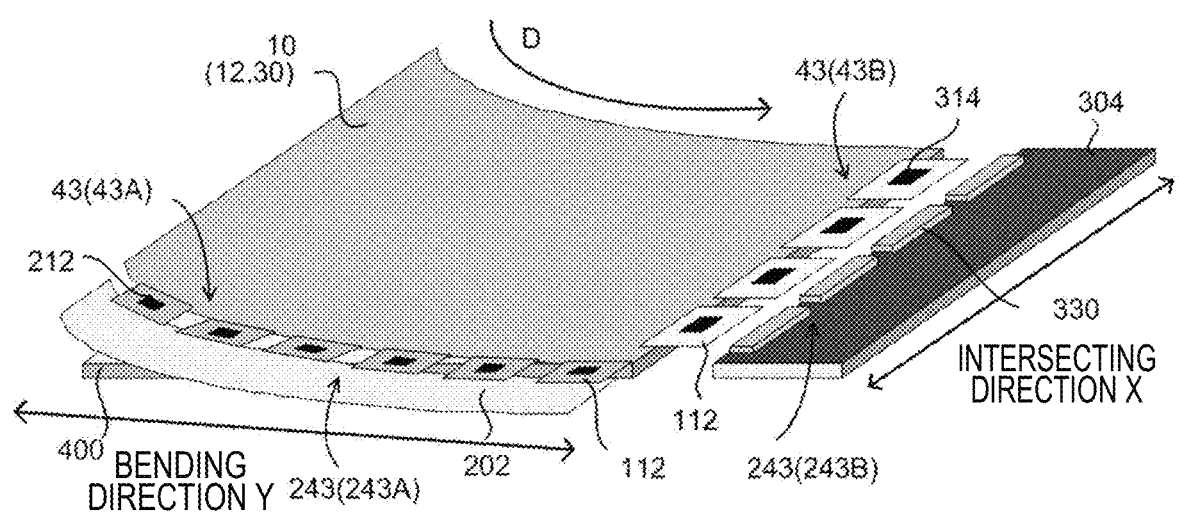
FIG. 7 is an explanatory diagram to explain an example of a manufacturing method of a radiation detector of the first exemplary embodiment.

The radiation detector 10 is then separated from the support body 400 as illustrated in FIG. 7. When separating by mechanical separation, as in the example illustrated in FIG. 7, separation is started at an opposite edge of the TFT substrate 12 to an edge to which the flexible cables 112 are connected, and the TFT substrate 12 is gradually peeled away from the support body 400 in the arrow D direction in FIG. 7 on progression toward from the start edge toward the edge to which the flexible cables 112 are connected. The radiation detector 10 is thereby obtained in a state in which the flexible cables 112 are connected thereto by performing such mechanical separation.

Note that the edge from which separation is started is preferably on edge intersecting the longest edge of the TFT substrate 12 as viewed in plan view. In other words, an edge along the bending direction Y in which bending occurs during separation is preferably the longest edge. In the present exemplary embodiment, the edge to which the drive substrate 202 is connected through the flexible cables 112 is longer than the edge to which the signal processing substrate 304 is connected through the flexible cables 112. Accordingly, separation is started at the opposite edge to the edge provided with the connection region 43 (43B).

In the present exemplary embodiment, after separating the TFT substrate 12 from the support body 400, the flexible cables 112 of the radiation detector 10 and the connectors 330 of the signal processing substrate 304 are electrically connected together. The radiation detector 10 of the example of the present exemplary embodiment illustrated in FIG. 3 to FIG. 5 is manufactured in this manner.

Note that the present exemplary embodiment is not limited thereto, and the above mechanical separation may be performed after the flexible cables 112 of the radiation detector 10 and the connectors 330 of the signal processing substrate 304 have been electrically connected together.

During mechanical separation, as illustrated in FIG. 6 and FIG. 7, the drive substrate 202 of the radiographic imaging device 1 of the present exemplary embodiment also bends in response to the bending of the TFT substrate 12 since the drive substrate 202 is a flexible substrate.

Note that when separating the TFT substrate 12 from the support body 400, due to the flexibility of the base member 11, the TFT substrate 12 bends readily. When the TFT substrate 12 bends greatly, there is a concern of the conversion layer 14 detaching from the TFT substrate 12 as a result of the TFT substrate 12 bending greatly. In particular, the end portion of the conversion layer 14 is liable to detach from the TFT substrate 12. Moreover, there is a concern of the conversion layer 14 detaching from the TFT substrate 12 due to bending of the TFT substrate 12 not only when separating the TFT substrate 12 from the support body 400, but also when the radiation detector 10 is handled on its own such as during manufacturing processes of the radiographic imaging device 1. To address this, in the radiation detector 10 of the present exemplary embodiment, the reinforcement substrate 40 that contains a material having a yield point and that has a higher rigidity than the base member 11 is provided to the first surface 19A, this being an opposite-side surface to the first surface 12A of the TFT substrate 12. Accordingly, the radiation detector 10 of the present exemplary embodiment is capable of suppressing sharp bending of the TFT substrate 12, enabling the conversion layer 14 to be suppressed from detaching from the TFT substrate 12.

Second Exemplary Embodiment

Figure 8:
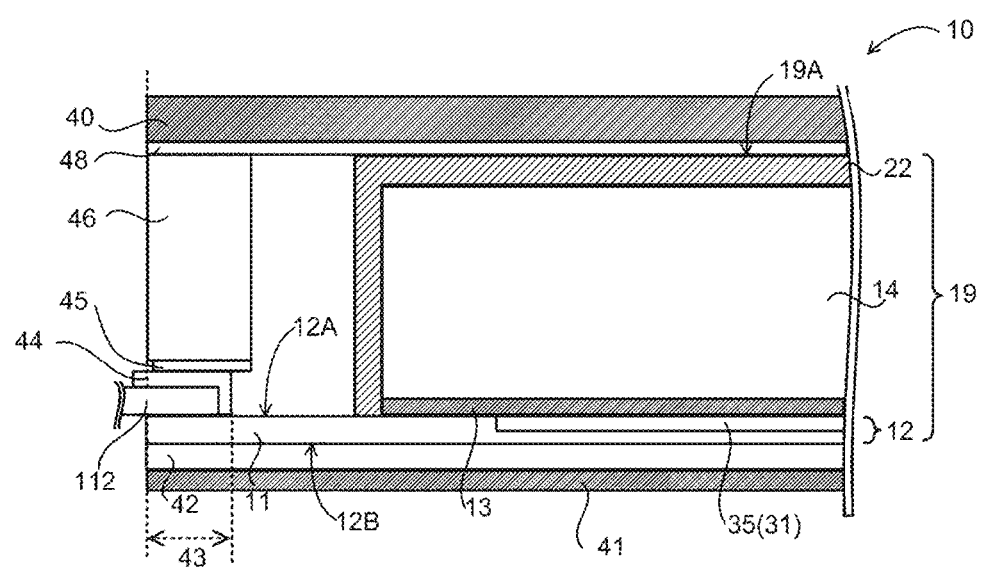
FIG. 8 is a cross-section illustrating an example of a radiation detector of a second exemplary embodiment.

Next, explanation follows regarding a second exemplary embodiment. FIG. 8 is a cross-section illustrating an example of a radiation detector 10 of the present exemplary embodiment.

As illustrated in FIG. 8, in the radiation detector 10 of the present exemplary embodiment, a reinforcement member 41 is provided to the second surface 12B of the TFT substrate 12. In the radiation detector 10 of the present exemplary embodiment, as illustrated in FIG. 8, the protective film 42 is provided between the TFT substrate 12 and the reinforcement member 41, similarly to in the exemplary embodiment described above.

Similarly to the reinforcement substrate 40, the reinforcement member 41 has a higher rigidity than the base member 11, such that dimensional change (deformation) with respect to force applied in a direction perpendicular to the first surface 12A is smaller than the dimensional change with respect to force applied in a direction perpendicular to the first surface 12B of the base member 11. The thickness of the reinforcement member 41 of the present exemplary embodiment is thicker than the thickness of the base member 11, and thinner than the thickness of the reinforcement substrate 40. The material employed for the reinforcement member 41 of the present exemplary embodiment is preferably a thermoplastic resin, and similar materials to those of the reinforcement substrate 40 may be employed. Note that the rigidity referred to here refers to the difficulty of bending the reinforcement member 41 and the base member 11, including the thicknesses of the reinforcement member 41 and the base member 11, with bending becoming more difficult the greater the rigidity.

In the radiation detector 10 of the present exemplary embodiment, a similar manufacturing method to the manufacturing method of the radiation detector 10 described above in the first exemplary embodiment may, for example, be employed to affix the reinforcement substrate 40 provided with the spacer 46 to the TFT substrate 12 provided with the stacked body 19, and then separate the TFT substrate 12 from the support body 400. The radiation detector 10 of the present exemplary embodiment can then be manufactured by performing coating or the like to provide the protective film 42 and the reinforcement member 41 on the second surface 12B of the TFT substrate 12.

In the radiation detector 10 of the present exemplary embodiment, the reinforcement member 41 that has a higher rigidity than the base member 11 is provided on the second surface 12B of the TFT substrate 12 that opposes the first surface 12A formed with the plural pixels 30. This enables the TFT substrate 12 to be further suppressed from bending greatly, thus enabling the conversion layer 14 to be suppressed from detaching from the TFT substrate 12, compared to the radiation detector 10 of the exemplary embodiment described above.

Moreover, for example, the TFT substrate 12 is susceptible to warping in cases in which the difference between the coefficient of thermal expansion of the conversion layer 14 and the coefficient of thermal expansion of the reinforcement substrate 40 is comparatively large. To address this, in the radiation detector 10 of the present exemplary embodiment, the TFT substrate 12 is sandwiched between the reinforcement substrate 40 and the reinforcement member 41, enabling warping of the TFT substrate 12 due to the difference in coefficients of thermal expansion and the like to be suppressed.

As described above, each of the radiation detectors 10 of the exemplary embodiments described above includes the TFT substrate 12 in which the plural pixels 30 configured to accumulate charges generated in response to light converted from radiation are formed on the pixel region 35 of the flexible base member 11, the conversion layer 14 provided on the first surface 12A, this being the surface provided with the pixel region 35 of the flexible base member 11, and configured to convert radiation into light, and the reinforcement substrate 40 provided on the first surface 19A, this being the opposite-side surface of the conversion layer 14 to the surface on the TFT substrate 12 side, and that contains a material having a yield point and that has a higher rigidity than the base member 11.

In the radiation detectors 10 of the exemplary embodiments described above, providing the reinforcement substrate 40 that contains a material having a yield point and that has a higher rigidity than the base member 11 on top of the conversion layer 14 enables sharp bending of the TFT substrate 12 to be suppressed. Accordingly, the radiation detectors 10 of the exemplary embodiments described above are each capable of suppressing the conversion layer 14 from detaching from the TFT substrate 12 when the radiation detector 10 is handled on its own.

Figure 9:
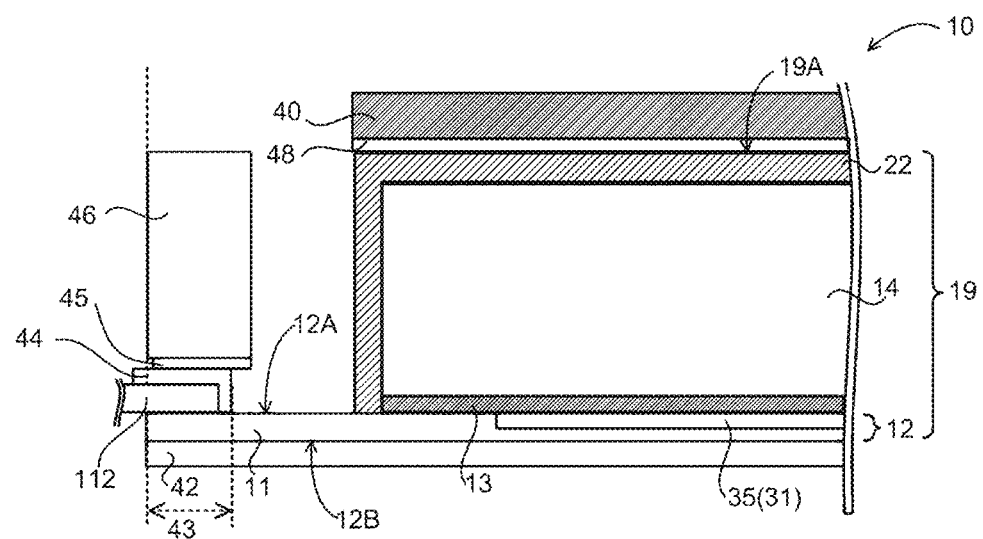
FIG. 9 is a cross-section illustrating another example of a radiation detector of an exemplary embodiment.

Note that the size of the reinforcement substrate 40 is not limited to that of the exemplary embodiments described above. For example, as in the example illustrated in FIG. 9, end portions (outer peripheries) of the reinforcement substrate 40 and the adhesion layer 48 may be provided at similar positions to an outer end portion (outer periphery) of the protective layer 22. Note that a wider region than the region where the conversion layer 14 covers the first surface 12A of the TFT substrate 12 is preferably covered by the reinforcement substrate 40, and a wider region than the region covering the entire upper face of the conversion layer 14 is more preferably covered by the reinforcement substrate 40.

Figure 10:
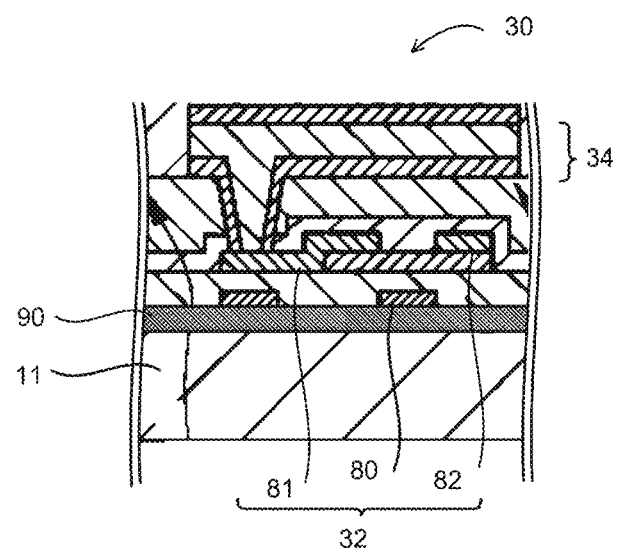
FIG. 10 is a cross-section illustrating a portion corresponding to a single pixel in another example of a radiation detector of an exemplary embodiment.

As in the example illustrated in FIG. 10, a layer 90 configured of an inorganic material is preferably provided between the base member 11 and the pixels 30, and in particular between the base member 11 and gate electrodes 80 of the TFTs 32 of the pixels 30. Examples of the inorganic material employed in the example illustrated in FIG. 10 include SiNx, SiOx, and the like. Drain electrodes 81 and source electrodes 82 of the TFTs 32 are formed in the same layer as each other, and the gate electrodes 80 are formed between the base member 11 and the layer formed with the drain electrodes 81 and the source electrodes. The layer 90 that is configured of an inorganic material is provided between the base member 11 and the gate electrodes 80.

In the exemplary embodiments described above, explanation has been given regarding embodiments in which the pixels 30 are arrayed in a two-dimensional matrix pattern as illustrated in FIG. 1. However, there is no limitation thereto, and, for example, the pixels 30 may be arrayed in one dimension, or may be arrayed in a honeycomb formation. The shape of the pixels is not limited, and the pixels may be rectangular or polygonal, for example hexagonal, in shape. Obviously the shape of the pixel array 31 (pixel region 35) is likewise not limited.

The shape and the like of the conversion layer 14 are also not limited to that of the exemplary embodiments described above. In the exemplary embodiments described above, explanation has been given regarding embodiments in which the shape of the conversion layer 14 is a rectangular shape similar to the shape of the pixel array 31 (pixel region 35). However, the shape of the conversion layer 14 does not have to be a similar shape to that of the pixel array 31 (pixel region 35). Moreover, instead of being rectangular, the shape of the pixel array 31 (pixel region 35) may for example be another polygonal shape, or may be circular.

Note that although explanation has been given regarding a manufacturing method of the radiation detector 10 in which the separation process is performed by mechanically separating the TFT substrate 12 from the support body 400, the separation method is not limited thereto. For example, the TFT substrate 12 may be separated by what is referred to as laser separation, in which a laser is irradiated onto an opposite-side surface of the support body 400 to the side formed with the TFT substrate 12. In such cases, the radiation detector 10 is still capable of suppressing the conversion layer 14 from detaching from the TFT substrate 12 when the radiation detector 10 is handled on its own after the TFT substrate 12 has been separated from the support body 400.

Note that in the radiation detectors 10 of the exemplary embodiments described above, either an irradiation side sampling (ISS) approach, in which radiation is irradiated from the TFT substrate 12 side, may be adopted, or a penetration side sampling (PSS) approach, in which radiation is irradiated from the conversion layer 14 side, may be adopted for the radiographic imaging device.

Figure 11:
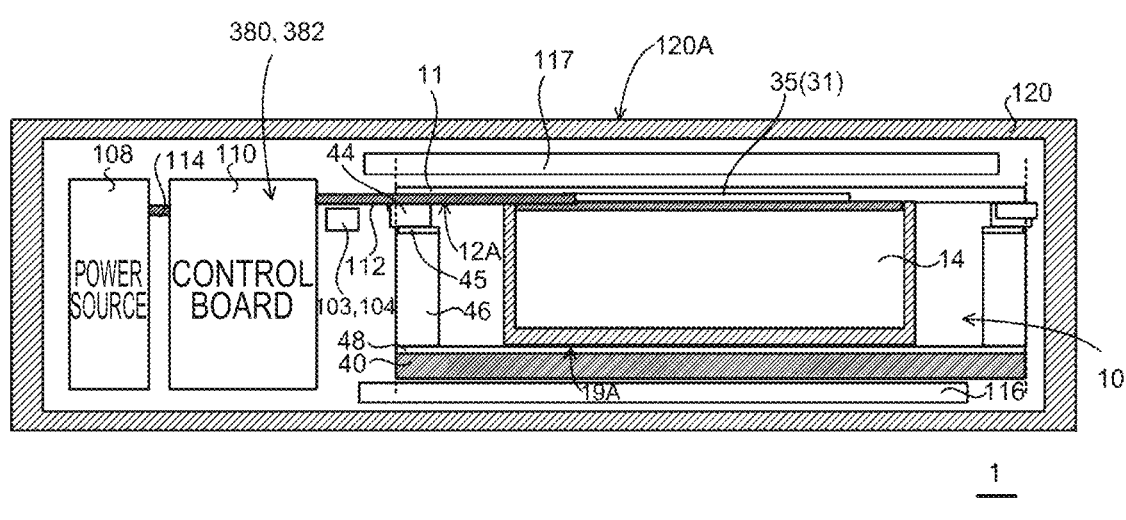
FIG. 11 is a cross-section illustrating an example of a radiographic imaging device applied with a radiation detector of an exemplary embodiment.

FIG. 11 is a cross-section illustrating an example of a state in which a radiographic imaging device 1 employing an ISS approach is applied with the radiation detector 10 of the first exemplary embodiment.

As illustrated in FIG. 11, the radiation detector 10, a power source section 108, and a control board 110 are arranged inside a case 120 along a direction intersecting a direction in which radiation is incident. In the radiation detector 10, the side of the pixel array 31 not provided with the conversion layer 14 opposes an imaging face 120A side of the case 120 that is irradiated with radiation that has passed through the imaging subject.

The case 120 is preferably lightweight, has a low absorption ratio of radiation R, in particular X-rays, and high rigidity, and is preferably configured from a material that has a sufficiently high elastic modulus. A material having a bending elastic modulus of at least 10,000 MPa is preferably employed as the material of the case 120. Examples of materials suitably employed as the material of the case 120 include carbon or carbon fiber reinforced plastic (CFRP) having a bending elastic modulus of around 20,000 MPa to 60,000 MPa.

During capture of radiographic images by the radiographic imaging device 1, a load is applied to the imaging face 120A of the case 120 from the imaging subject. If the rigidity of the case 120 were insufficient, the load from the imaging subject would cause the TFT substrate 12 to bend, and there would be a concern of faults occurring such as damage to the pixels 30. Housing the radiation detector 10 inside the case 120 configured from a material having a bending elastic modulus of at least 10,000 MPa enables bending of the TFT substrate 12 due to the load from the imaging subject to be suppressed.

The control board 110 is a substrate formed with image memory 380 configured to store image data corresponding to the charges read from the pixels 30 of the pixel array 31, a control section 382 configured to control reading of the charges from the pixels 30, and the like. The control board 110 is electrically connected to the pixels 30 of the pixel array 31 through the flexible cables 112 including the plural signal lines. Note that in the radiographic imaging device 1 illustrated in FIG. 11, the drive section 103 that controls the switching states of the TFTs 32 of the pixels 30 under the control of the control section 382, and the signal processing section 104 that generates and outputs image data corresponding to the charges read from the pixels 30 are configured by chip-on-film (COF) provided on the flexible cables 112. However, at least one out of the drive section 103 or the signal processing section 104 may be formed on the control board 110.

A power source line 114 connects the control board 110 to the power source section 108 so as to supply electrical power to the image memory 380, the control section 382, and the like formed on the control board 110.

A sheet 116 is provided inside the case 120 of the radiographic imaging device 1 illustrated in FIG. 11 on the side where radiation that has passed through the radiation detector 10 is emitted. The sheet 116 may, for example, be a copper sheet. A copper sheet does not readily generate secondary radiation from incident radiation, and thus has a function of preventing scattering toward the rear, namely toward the conversion layer 14 side. Note that the sheet 116 at least covers the entire surface on the radiation emission side of the conversion layer 14 and preferably covers the entire conversion layer 14.

A protective layer 117 is further provided inside the case 120 of the radiographic imaging device 1 illustrated in FIG. 11 on the side to which radiation is incident (the imaging face 120A side). The protective layer 117 may, for example, be configured by a moisture-proof film such as an ALPET (registered trademark) sheet in which an aluminum layer such as an aluminum foil is bonded to an insulating sheet (film), or an insulating sheet such as a Parylene (registered trademark) film or polyethylene terephthalate. The protective layer 117 has a moisture-proof function and an antistatic function with respect to the pixel array 31. Accordingly, the protective layer 117 preferably covers at least the entire surface of the pixel array 31 on the side to which the radiation is incident, and preferably covers the entire surface of the TFT substrate 12 on the side to which the radiation is incident.

Note that FIG. 11 illustrates an embodiment in which both the power source section 108 and the control board 110 are provided on one side of the radiation detector 10, specifically on the side of one edge of the rectangular pixel array 31. However, the positions at which the power source section 108 and the control board 110 are provided are not limited to those of the embodiment illustrated in FIG. 11. For example, the power source section 108 and the control board 110 may be provided distributed between two opposing edges of the pixel array 31, or may be provided distributed between two adjacent edges of the pixel array 31.

Figure 12:
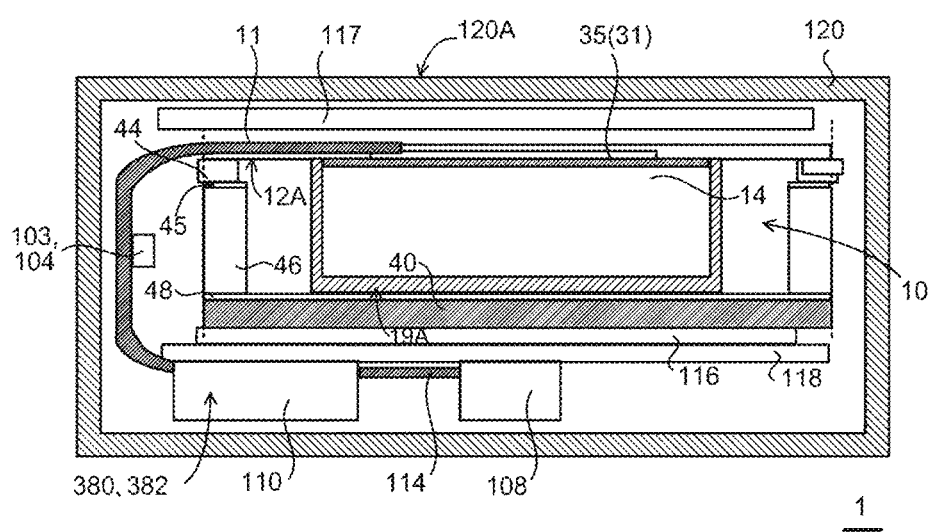
FIG. 12 is a cross-section illustrating another example of a radiographic imaging device applied with a radiation detector of an exemplary embodiment.

FIG. 12 is a cross-section illustrating another example of a state in which the radiation detector 10 of the first exemplary embodiment is applied to a radiographic imaging device 1 employing an ISS approach.

As illustrated in FIG. 12, the power source section 108 and the control board 110 are provided arranged inside the case 120 in a direction intersecting the direction in which radiation is incident, and the radiation detector 10 and the power source section 108 and control board 110 are provided arranged inside the case 120 along the direction in which radiation is incident.

In the radiographic imaging device 1 illustrated in FIG. 12, a base 118 is provided between the control board 110 and power source section 108 and the sheet 116 to support the radiation detector 10 and the control board 110. For example, carbon or the like is employed for the base 118.

The configurations and manufacturing methods of the radiation detector 10 and so on of the exemplary embodiments described above are merely examples thereof, and obviously modifications are possible according to circumstances within a range not departing from the spirit of the present invention.

Other Exemplary Embodiments

First, explanation follows regarding other exemplary embodiments of the reinforcement substrate 40, with reference to FIG. 13 to FIG. 34.

In cases in which the conversion layer 14 is formed using a vapor phase deposition method, as illustrated in FIG. 13 to FIG. 34, the conversion layer 14 is formed with a slope with a gradually decreasing thickness on progression toward an outer edge thereof. In the following explanation, a central region of the conversion layer 14 where the thickness may be regarded as substantially constant if manufacturing error and measurement error are ignored is referred to as a central portion 14A. An outer peripheral region of the conversion layer 14 where the thickness is, for example, not more than 90% of the average thickness of the central portion 14A of the conversion layer 14 is referred to as a peripheral edge portion 14B. Namely, the conversion layer 14 includes a sloping face that slopes with respect to the TFT substrate 12 at the peripheral edge portion 14B.

As illustrated in FIG. 13 to FIG. 34, an adhesion layer 60, a reflective layer 62, a bonding layer 64, the protective layer 22, and the adhesion layer 48 may be provided between the conversion layer 14 and the reinforcement substrate 40.

The adhesion layer 60 covers the entire front surface of the conversion layer 14, including the central portion 14A and the peripheral edge portion 14B of the conversion layer 14. The adhesion layer 60 includes a function to fix the reflective layer 62 onto the conversion layer 14. The adhesion layer 60 preferably has light-transmitting properties. Examples of materials that may be employed for the adhesion layer 60 include acrylic-based adhesives, hot-melt-based adhesives, silicone-based bonding agents, and the like. Examples of acrylic-based adhesives include, for example, urethane acrylates, acrylic resin acrylates, epoxy acrylates, and the like. Examples of hot-melt-based adhesives include thermoplastic plastics such as copolymer resins of ethylene vinyl acetate (EVA), copolymer resins of ethylene and acrylic acid (EAA), copolymer resins of ethylene and ethyl acrylate (EEA), copolymers of ethylene/methyl methacrylate (EMMA), and the like. The thickness of the adhesion layer 60 is preferably from 2 µm to 7 µm. Making the thickness of the adhesion layer 60 no less than 2 µm enables the effect of fixing the reflective layer 62 onto the conversion layer 14 to be sufficiently exhibited. Furthermore, this also enables the risk of an air layer being formed between the conversion layer 14 and the reflective layer 62 to be suppressed. Were an air layer to be formed between the conversion layer 14 and the reflective layer 62, then there would be concern that multiple reflection of the light emitted from the conversion layer 14 might occur, with the light being repeatedly reflected between the air layer and the conversion layer 14, and between the air layer and the reflective layer 62. Moreover, making the thickness of the adhesion layer 60 no greater than 7 µm enables a reduction in modulation transfer function (MTF) and detective quantum efficiency (DQE) to be suppressed.

The reflective layer 62 covers the entire front surface of the adhesion layer 60. The reflective layer 62 has a function of reflecting light converted by the conversion layer 14. The reflective layer 62 is preferably configured from an organic material. Examples of materials that may be employed for the reflective layer 62 include white PET, $TiO_2$, $Al_2O_3$, foamed white PET, polyester-based high reflectivity sheets, specular reflective aluminum, and the like. The thickness of the reflective layer 62 is preferably from 10 µm to 40 µm.

The bonding layer 64 covers the entire front surface of the reflective layer 62. An end portion of the bonding layer 64 extends as far as the front surface of the TFT substrate 12. Namely, the bonding layer 64 is bonded to the TFT substrate 12 at this end portion. The bonding layer 64 has a function to fix the reflective layer 62 and the protective layer 22 to the conversion layer 14. The same materials may be employed for the material of the bonding layer 64 as the materials that may be employed for the adhesion layer 60. However, the bonding strength of the bonding layer 64 is preferably greater than the bonding strength of the adhesion layer 60.

The protective layer 22 covers the entire front surface of the bonding layer 64. Namely, the protective layer 22 is provided in a state covering the entirety of the conversion layer 14, and an end portion of the protective layer 22 also covers a portion of the TFT substrate 12. The protective layer 22 functions as a moisture-proof film to prevent the ingress of moisture into the conversion layer 14. Examples of materials that may be employed as the material of the protective layer 22 include organic films containing an organic material such as PET, PPS, OPP, PEN, PI, and the like. Moreover, an ALPET (registered trademark) sheet may be employed as the protective layer 22.

The reinforcement substrate 40 is provided on the front surface of the protective layer 22, with the adhesion layer 48 interposed therebetween. The same materials may, for example, be employed for the material of the adhesion layer 48 as the materials that may be employed for the adhesion layer 60 and the adhesion layer 48.

Figure 13:
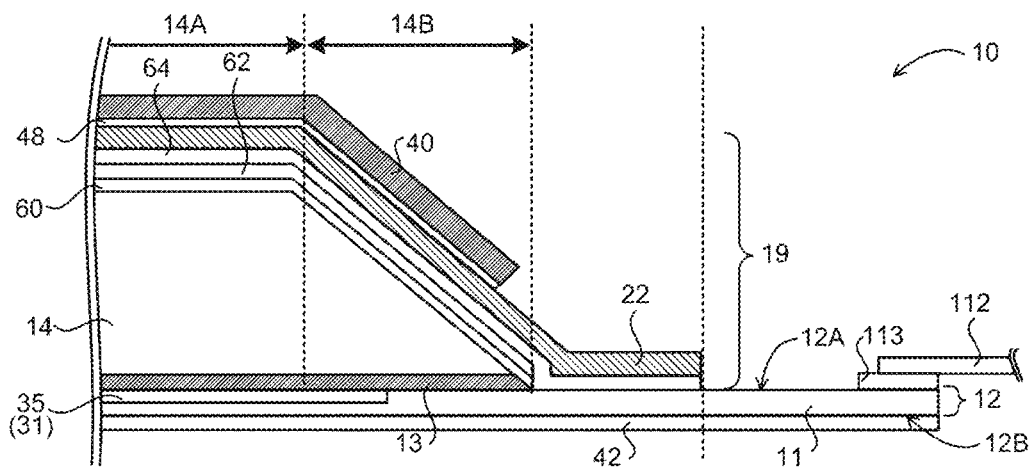
FIG. 13 is a cross-section illustrating an example of configuration of a radiation detector of an exemplary embodiment of technology disclosed herein.

In the example illustrated in FIG. 13, the reinforcement substrate 40 extends over regions corresponding to the central portion 14A and the peripheral edge portion 14B of the conversion layer 14, with an outer peripheral portion of the reinforcement substrate 40 angled so as to follow the slope of the peripheral edge portion 14B of the conversion layer 14. The reinforcement substrate 40 is bonded to the protective layer 22 through the adhesion layer 48 at both the region corresponding to the central portion 14A and the region corresponding to the peripheral edge portion 14B of the conversion layer 14. In the example illustrated in FIG. 13, an end portion of the reinforcement substrate 40 is disposed at the region corresponding to the peripheral edge portion 14B of the conversion layer 14.

Figure 14:
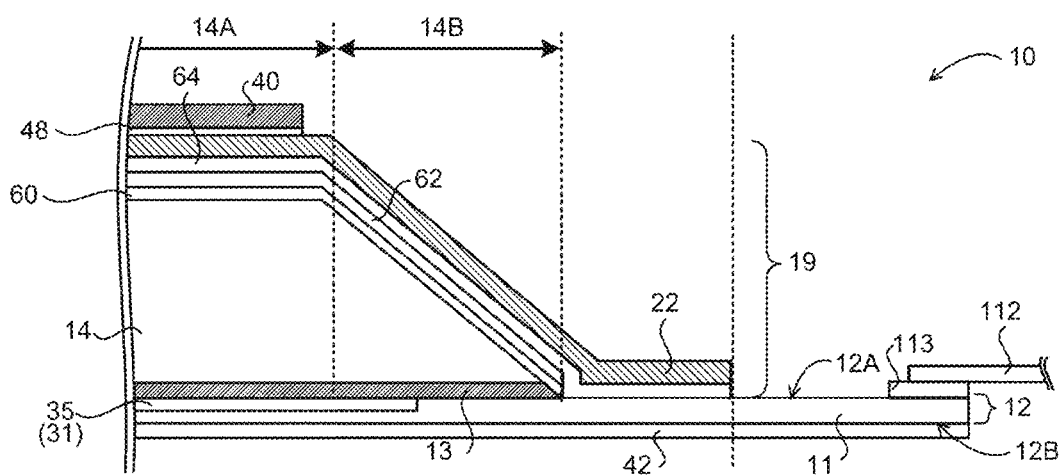
FIG. 14 is a cross-section illustrating an example of configuration of a radiation detector of an exemplary embodiment of technology disclosed herein.

As illustrated in FIG. 14, the reinforcement substrate 40 may be provided only at the region corresponding to the central portion 14A of the conversion layer 14. In such cases, the reinforcement substrate 40 is bonded to the protective layer 22 through the adhesion layer 48 at the region corresponding to the central portion 14A of the conversion layer 14.

Figure 15:
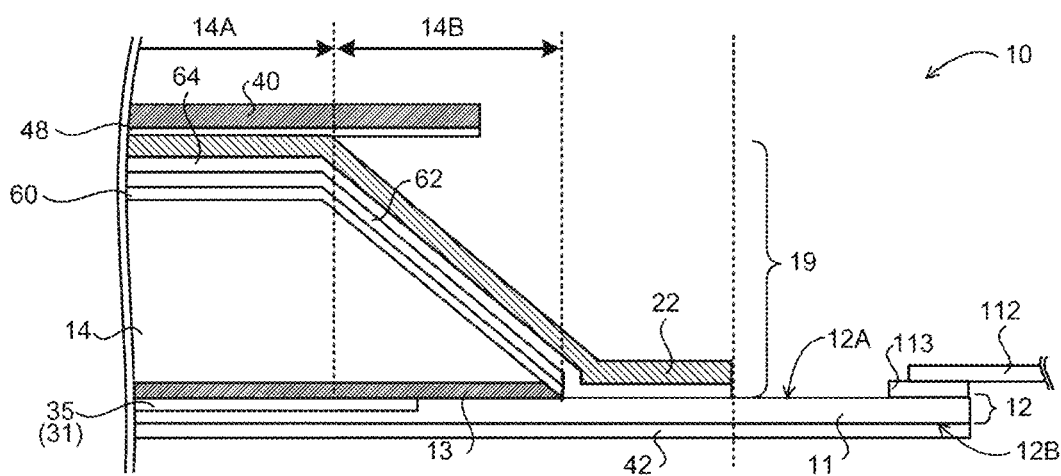
FIG. 15 is a cross-section illustrating an example of configuration of a radiation detector of an exemplary embodiment of technology disclosed herein.

As illustrated in FIG. 15, in cases in which the reinforcement substrate 40 extends over the regions corresponding to both the central portion 14A and the peripheral edge portion 14B of the conversion layer 14, the reinforcement substrate 40 may be configured without providing an angled portion to follow the slope of the outer peripheral portion of the conversion layer 14. In such cases, the reinforcement substrate 40 is bonded to the protective layer 22 through the adhesion layer 48 at the region corresponding to the central portion 14A of the conversion layer 14. A space corresponding to the slope of the peripheral edge portion 14B of the conversion layer 14 is formed between the conversion layer 14 (the protective layer 22) and the reinforcement substrate 40 at the region corresponding to the peripheral edge portion 14B of the conversion layer 14.

Note that the flexible cable 112 is connected to terminals 113 provided in a connection region at the outer peripheral portion of the TFT substrate 12. The TFT substrate 12 is connected to a control board (the control board 110, see FIG. 47, etc.) through the flexible cable 112. There is a concern that the flexible cable 112 might detach from the TFT substrate 12 or positional misalignment might arise were bending of the TFT substrate 12 to occur. In such cases it is necessary to perform a task to reconnect the flexible cable 112 and the TFT substrate 12. This task to reconnect the flexible cable 112 and the TFT substrate 12 is called re-work. As illustrated in FIG. 13 to FIG. 15, by arranging the end portion of the reinforcement substrate 40 at the inside of the end portion of the conversion layer 14, re-work can be performed more easily than in cases in which the reinforcement substrate 40 extends to the vicinity of the connection region.

As illustrated in FIG. 16 to FIG. 19, the end portion of the reinforcement substrate 40 may be disposed at the outer side of the end portion of the conversion layer 14, and may be provided so as to be aligned with the end portions of the bonding layer 64 and the protective layer 22 that both extend over the TFT substrate 12. Note that there is no need for the position of the end portion of the reinforcement substrate 40 to align exactly with the position of the end portions of the bonding layer 64 and the protective layer 22.

Figure 16:
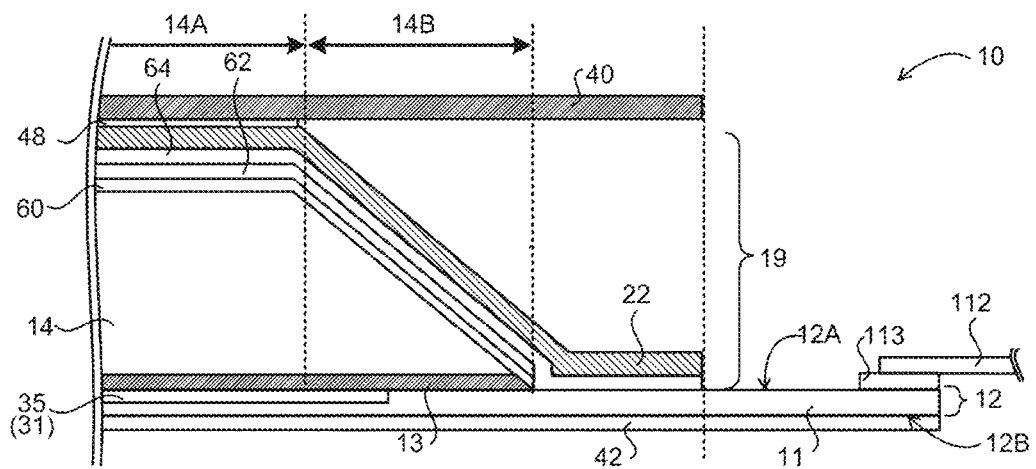
FIG. 16 is a cross-section illustrating an example of configuration of a radiation detector of an exemplary embodiment of technology disclosed herein.

In the example illustrated in FIG. 16, the reinforcement substrate 40 is bonded to the protective layer 22 through the adhesion layer 48 at the region corresponding to the central portion 14A of the conversion layer 14, and a space corresponding to the slope at the peripheral edge portion 14B of the conversion layer 14 is formed between the conversion layer 14 (the protective layer 22) and the reinforcement substrate 40 at the region corresponding to the peripheral edge portion 14B of the conversion layer 14 and also at a region at the outer side thereof.

Figure 17:
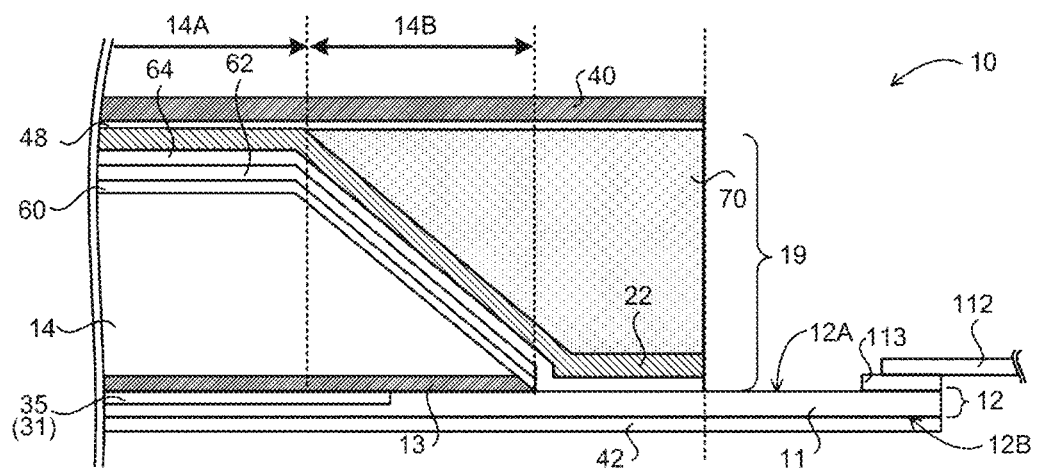
FIG. 17 is a cross-section illustrating an example of configuration of a radiation detector of an exemplary embodiment of technology disclosed herein.

In the example illustrated in FIG. 17, a filler 70 is provided in the space formed between the conversion layer 14 (the protective layer 22) and the reinforcement substrate 40 at the region corresponding to the peripheral edge portion 14B of the conversion layer 14 and also at the region at the outer side thereof. The material of the filler 70 is not particularly limited, and examples of materials that may be employed therefor include resins. Note that in the example illustrated in FIG. 17, the adhesion layer 48 is provided across the entire region between the reinforcement substrate 40 and the filler 70 in order to fix the reinforcement substrate 40 to the filler 70.

The method of forming the filler 70 is not particularly limited. For example, after forming the adhesion layer 48 and the reinforcement substrate 40 in sequence on top of the conversion layer 14 covered by the adhesion layer 60, the reflective layer 62, the bonding layer 64, and the protective layer 22, flowable filler 70 may be poured into the space formed between the conversion layer 14 (the protective layer 22) and the reinforcement substrate 40, and the filler 70 then cured. Alternatively, for example, after forming the conversion layer 14, the adhesion layer 60, the reflective layer 62, the bonding layer 64, and the protective layer 22 in sequence on top of the TFT substrate 12, the filler 70 may be formed, and the adhesion layer 48 and the reinforcement substrate 40 may then be formed in sequence so as to cover the conversion layer 14 covered by the adhesion layer 60, the reflective layer 62, the bonding layer 64, and the protective layer 22, and also cover the filler 70.

By filling the filler 70 into the space formed between the conversion layer 14 (the protective layer 22) and the reinforcement substrate 40 in this manner, the reinforcement substrate 40 can be better suppressed from detaching from the conversion layer 14 (the protective layer 22) than in the embodiment illustrated in FIG. 16. Furthermore, due to adopting a structure in which the conversion layer 14 is fixed to the TFT substrate 12 by both the reinforcement substrate 40 and the filler 70, the conversion layer 14 can be suppressed from detaching from the TFT substrate 12.

Figure 18:
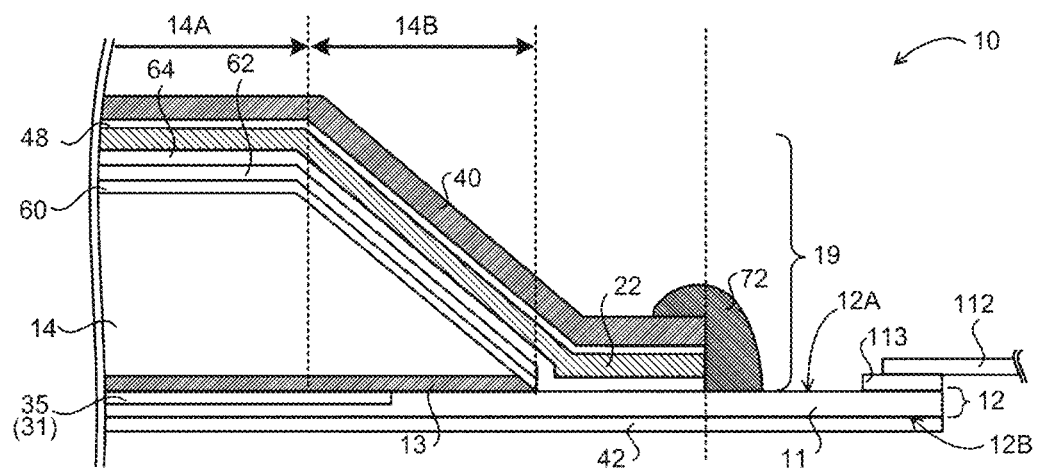
FIG. 18 is a cross-section illustrating an example of configuration of a radiation detector of an exemplary embodiment of technology disclosed herein.

In the example illustrated in FIG. 18, the outer peripheral portion of the reinforcement substrate 40 is angled so as to follow the slope of the peripheral edge portion 14B of the conversion layer 14, and so as also to cover the portions of the bonding layer 64 and the protective layer 22 that cover over the TFT substrate 12. Moreover, the end portion of the reinforcement substrate 40 and the end portions of the bonding layer 64 and the protective layer 22 are aligned with each other. Note that there is no need for the position of the end portion of the reinforcement substrate 40 to align exactly with the position of the end portions of the bonding layer 64 and the protective layer 22.

The end portions of the reinforcement substrate 40, the adhesion layer 48, the protective layer 22, and the bonding layer 64 are sealed with a sealing member 72. The sealing member 72 is preferably provided in a region spanning from the front surface of the TFT substrate 12 to the front surface of the reinforcement substrate 40, and in a region not covering the pixel region 35. Resins may be employed as the material of the sealing member 72, and thermoplastic resins are particularly preferably employed therefor. Specifically, glues such as acrylic glues, urethane based glues, and the like may be employed as the sealing member 72. The reinforcement substrate 40 has a higher rigidity than that of the protective layer 22, and there is a concern that restoring force due to the angle attempting to straighten out at the angled portion of the reinforcement substrate 40 might act to cause the protective layer 22 to detach therefrom. Sealing the end portions of the reinforcement substrate 40, the adhesion layer 48, the protective layer 22, and the bonding layer 64 using the sealing member 72 enables such detachment of the protective layer 22 to be suppressed.

Figure 19:
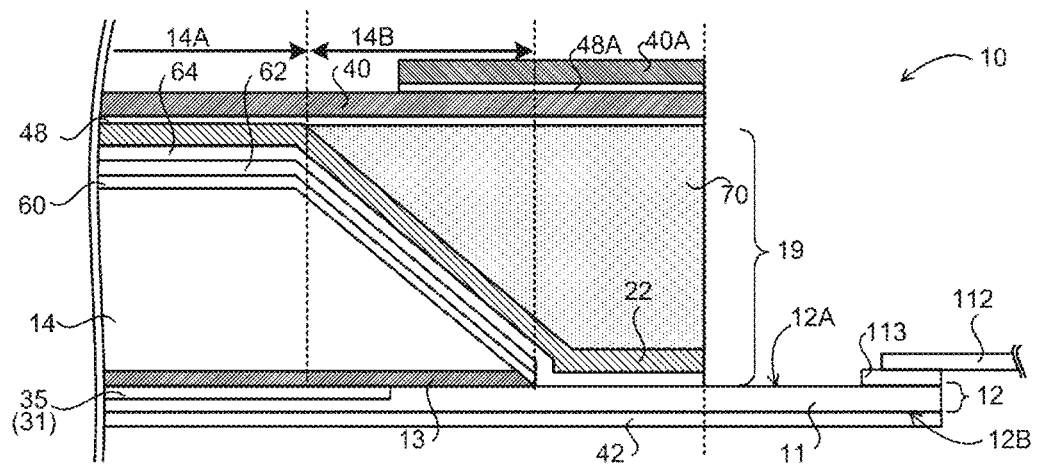
FIG. 19 is a cross-section illustrating an example of configuration of a radiation detector of an exemplary embodiment of technology disclosed herein.

Similarly to in the embodiment illustrated in FIG. 17, in the example illustrated in FIG. 19, the filler 70 is provided in a space formed between the conversion layer 14 (the protective layer 22) and the reinforcement substrate 40 at the region corresponding to the peripheral edge portion 14B of the conversion layer 14 and also at the region at the outer side thereof. Moreover, at the region corresponding to the end portion of the conversion layer 14, an additional and separate reinforcement substrate 40A is stacked on the front surface of the reinforcement substrate 40 with an adhesion layer 48A interposed therebetween. More specifically, the reinforcement substrate 40A is provided at a region straddling the end portion (outer edge, edge) of the conversion layer 14. The reinforcement substrate 40A may be configured from the same materials as the reinforcement substrate 40. In the radiation detector 10, the amount of bending of the TFT substrate 12 is comparatively large at the end portion of the conversion layer 14. Forming a multi-layer structure using the reinforcement substrates 40 and 50A at the region corresponding to the end portion of the conversion layer 14 enables the effect of suppressing bending of the TFT substrate 12 at the end portion of the conversion layer 14 to be enhanced.

As illustrated in FIG. 16 to FIG. 19, in cases in which the end portion of the reinforcement substrate 40 is disposed further to the outer side than the end portion of the conversion layer 14 and is provided so as to be aligned with the end portions of the bonding layer 64 and the protective layer 22, re-work can also be performed more easily than in cases in which the reinforcement substrate 40 extends as far as the vicinity of the connection region.

As illustrated in FIG. 20 to FIG. 23, a configuration may be adopted in which the end portion of the reinforcement substrate 40 is provided so as to be positioned further toward the outer side than the end portions of the bonding layer 64 and the protective layer 22 that extend as far as on top of the TFT substrate 12, and in a state positioned at the inner side of the end portion of the TFT substrate 12.

Figure 20:
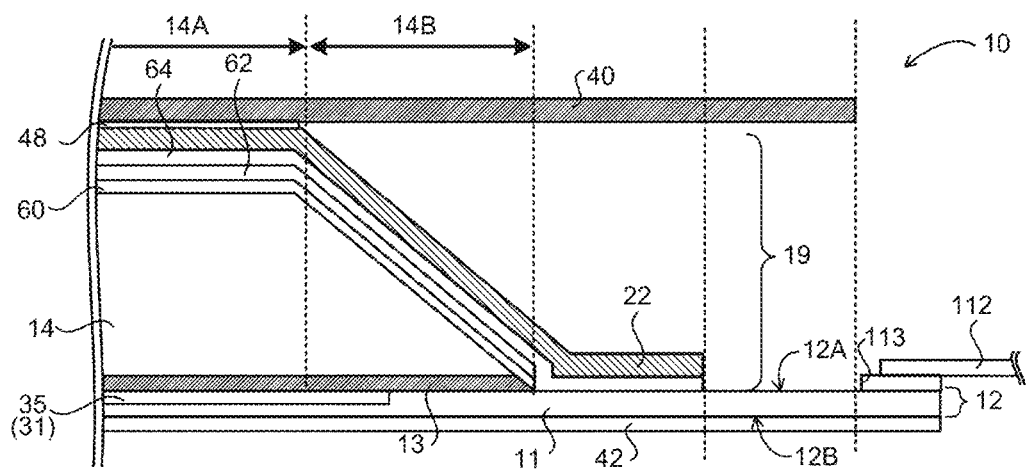
FIG. 20 is a cross-section illustrating an example of configuration of a radiation detector of an exemplary embodiment of technology disclosed herein.

In the example illustrated in FIG. 20, the reinforcement substrate 40 is bonded to the protective layer 22 through the adhesion layer 48 at the region corresponding to the central portion 14A of the conversion layer 14. At the region corresponding to the peripheral edge portion 14B of the conversion layer 14 and also at the region at the outer side thereof, a space corresponding to the slope of the peripheral edge portion 14B of the conversion layer 14 is formed between the conversion layer 14 (the protective layer 22) and the reinforcement substrate 40, and between the TFT substrate 12 and the reinforcement substrate 40.

Figure 21:
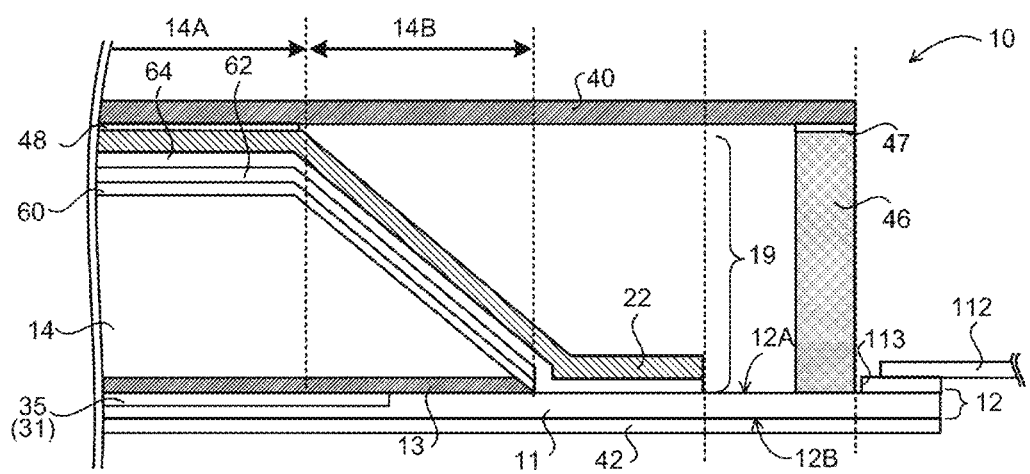
FIG. 21 is a cross-section illustrating an example of configuration of a radiation detector of an exemplary embodiment of technology disclosed herein.

In the example illustrated in FIG. 21, the end portion of the reinforcement substrate 40 is supported by the spacer 46. Namely, one end of the spacer 46 is connected to the first surface 12A of the TFT substrate 12, and the other end of the spacer 46 is connected to the end portion of the reinforcement substrate 40 through a bonding layer 47. By using the spacer 46 to support the end portion of the reinforcement substrate 40 that extends so as to form a space between itself and the TFT substrate 12, detachment of the reinforcement substrate 40 can be suppressed. Moreover, the bending suppression effect from the reinforcement substrate 40 can be caused to act as far as the vicinity of the end portion of the TFT substrate 12. Note that instead of providing the spacer 46, or in addition to providing the spacer 46, a filler may be filled into the space formed between the conversion layer 14 (the protective layer 22) and the reinforcement substrate 40, and between the TFT substrate 12 and the reinforcement substrate 40, in a similar manner to the example illustrated in FIG. 17.

Figure 22:
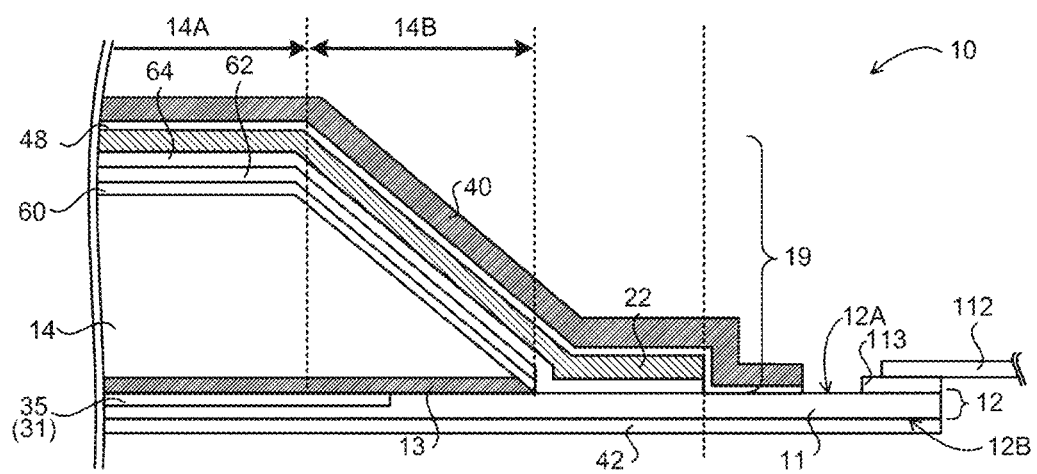
FIG. 22 is a cross-section illustrating an example of configuration of a radiation detector of an exemplary embodiment of technology disclosed herein.

In the example illustrated in FIG. 22, the outer peripheral portion of the reinforcement substrate 40 is angled so as to follow the slope at the peripheral edge portion 14B of the conversion layer 14, and covers the portion where the bonding layer 64 and the protective layer 22 cover over the TFT substrate 12 and also covers over the TFT substrate 12 at the outer side thereof. Namely, the end portions of the bonding layer 64 and the protective layer 22 are sealed by the reinforcement substrate 40. The portion of the reinforcement substrate 40 that extends over the TFT substrate 12 is bonded to the TFT substrate 12 through the adhesion layer 48. By covering the end portions of the bonding layer 64 and the protective layer 22 using the reinforcement substrate 40 in this manner, detachment of the protective layer 22 can be suppressed. Note that the sealing member 72 may be employed to seal the end portion of the reinforcement substrate 40, in a similar manner to the example illustrated in FIG. 18.

Figure 23:
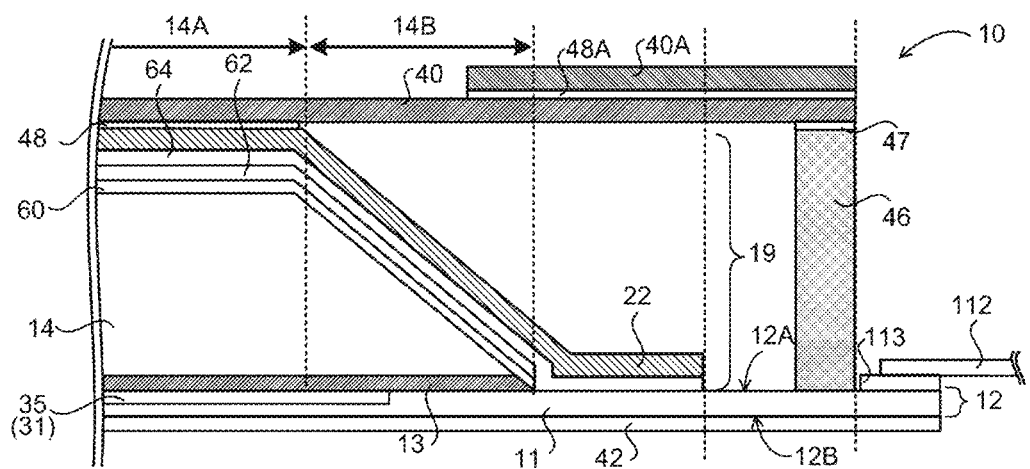
FIG. 23 is a cross-section illustrating an example of configuration of a radiation detector of an exemplary embodiment of technology disclosed herein.

The example illustrated in FIG. 23 is an embodiment in which the end portion of the reinforcement substrate 40 is supported by the spacer 46, and an additional and separate reinforcement substrate 40A is stacked on the front surface of the reinforcement substrate 40 at the region corresponding to the end portion of the conversion layer 14, with the adhesion layer 48A interposed therebetween. More specifically, the reinforcement substrate 40A is provided at a region straddling the end portion (outer edge, edge) of the conversion layer 14. The reinforcement substrate 40A may be configured from the same materials as the reinforcement substrate 40. In the radiation detector 10, the amount of bending of the TFT substrate 12 is comparatively large at the end portion of the conversion layer 14. Forming a multi-layer structure using the reinforcement substrates 40 and 40A at the region corresponding to the end portion of the conversion layer 14 enables the effect of suppressing bending of the TFT substrate 12 at the end portion of the conversion layer 14 to be enhanced. Note that instead of providing the spacer 46, the filler 70 may be filled into the space formed between the conversion layer 14 (the protective layer 22) and the reinforcement substrate 40, and between the TFT substrate 12 and the reinforcement substrate 40, in a similar manner to the example illustrated in FIG. 17.

As illustrated in FIG. 24 to FIG. 28, the end portion of the reinforcement substrate 40 may be provided so as to be aligned with the end portion of the TFT substrate 12. Note that there is no need for the position of the end portion of the reinforcement substrate 40 to align exactly with the position of the end portion of the TFT substrate 12.

Figure 24:
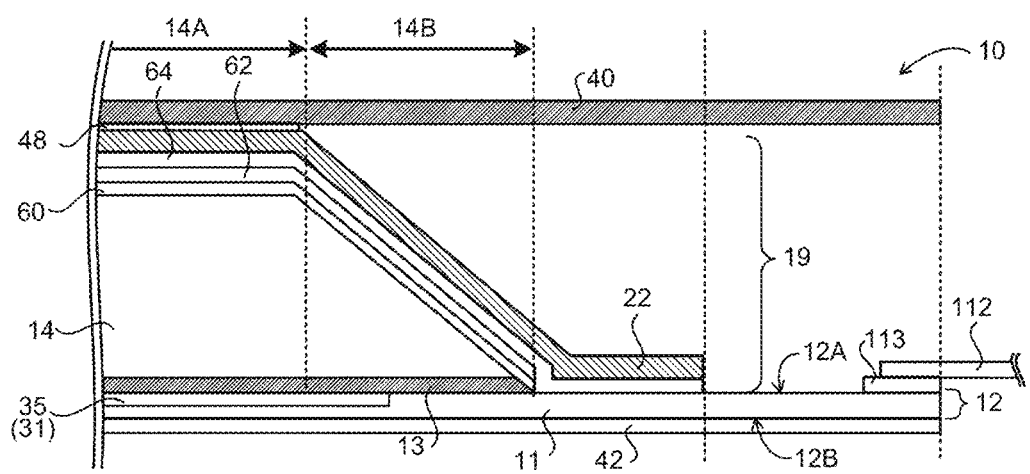
FIG. 24 is a cross-section illustrating an example of configuration of a radiation detector of an exemplary embodiment of technology disclosed herein.

In the example illustrated in FIG. 24, the reinforcement substrate 40 is bonded to the protective layer 22 through the adhesion layer 48 at the region corresponding to the central portion 14A of the conversion layer 14. A space corresponding to the slope of the peripheral edge portion 14B of the conversion layer 14 is formed between the conversion layer 14 (the protective layer 22) and the reinforcement substrate 40, and between the TFT substrate 12 and the reinforcement substrate 40, at the region corresponding to the peripheral edge portion 14B of the conversion layer 14 and also at the region at the outer side thereof.

Figure 25:
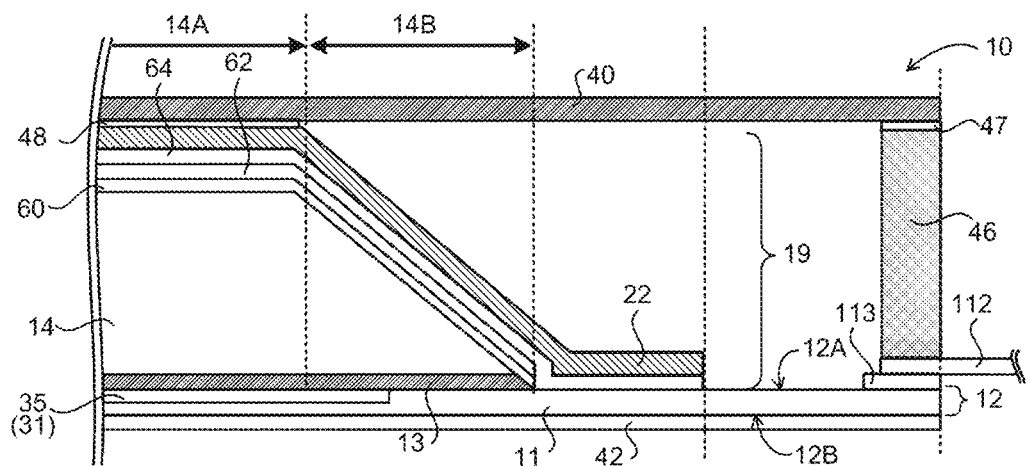
FIG. 25 is a cross-section illustrating an example of configuration of a radiation detector of an exemplary embodiment of technology disclosed herein.

In the example illustrated in FIG. 25, the end portion of the reinforcement substrate 40 is supported by the spacer 46. Namely, one end of the spacer 46 is connected to the flexible cable 112 provided at the end portion of the TFT substrate 12, and the other end of the spacer 46 is connected to the end portion of the reinforcement substrate 40 through the bonding layer 47. By using the spacer 46 to support the end portion of the reinforcement substrate 40 that extends so as to form a space between itself and the TFT substrate 12, detachment of the reinforcement substrate 40 can be suppressed. Moreover, the bending suppression effect from the reinforcement substrate 40 can be caused to act as far as the vicinity of the end portion of the TFT substrate 12.

Figure 26:
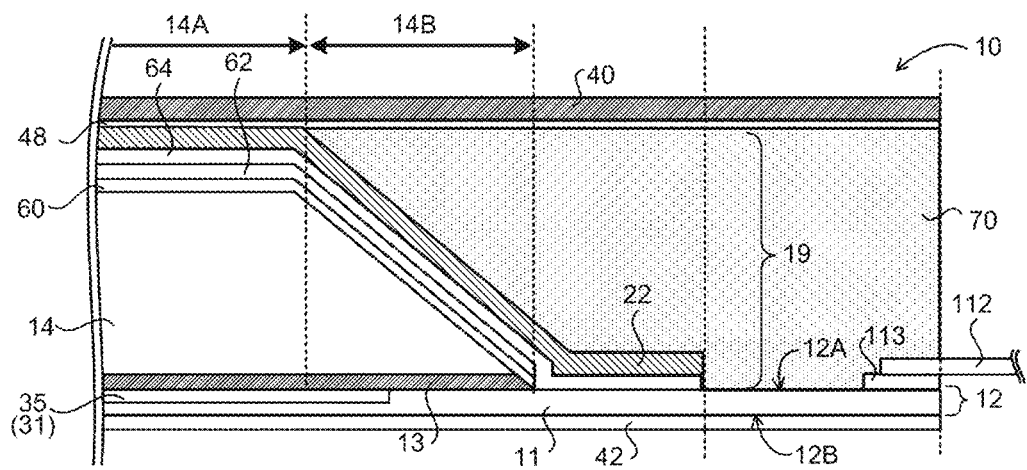
FIG. 26 is a cross-section illustrating an example of configuration of a radiation detector of an exemplary embodiment of technology disclosed herein.

In the example illustrated in FIG. 26, the space formed between the conversion layer 14 (the protective layer 22) and the reinforcement substrate 40, and between the TFT substrate 12 and the reinforcement substrate 40, is filled by the filler 70. In the present exemplary embodiment, the connection portions between the flexible cable 112 and the terminals 113 are covered by the filler 70. By thus filling the space formed between the conversion layer 14 (the protective layer 22) and the reinforcement substrate 40, and between the TFT substrate 12 and the reinforcement substrate 40, with the filler 70, the reinforcement substrate 40 can be better suppressed from detaching from the conversion layer 14 (the protective layer 22) than in the embodiment illustrated in FIG. 24. Furthermore, due to the structure in which the conversion layer 14 is fixed to the TFT substrate 12 by both the reinforcement substrate 40 and the filler 70, the conversion layer 14 can be suppressed from detaching from the TFT substrate 12. Moreover, since the connection portions between the flexible cable 112 and the terminals 113 are covered by the filler 70, detachment of the flexible cable 112 can also be suppressed.

Figure 27:
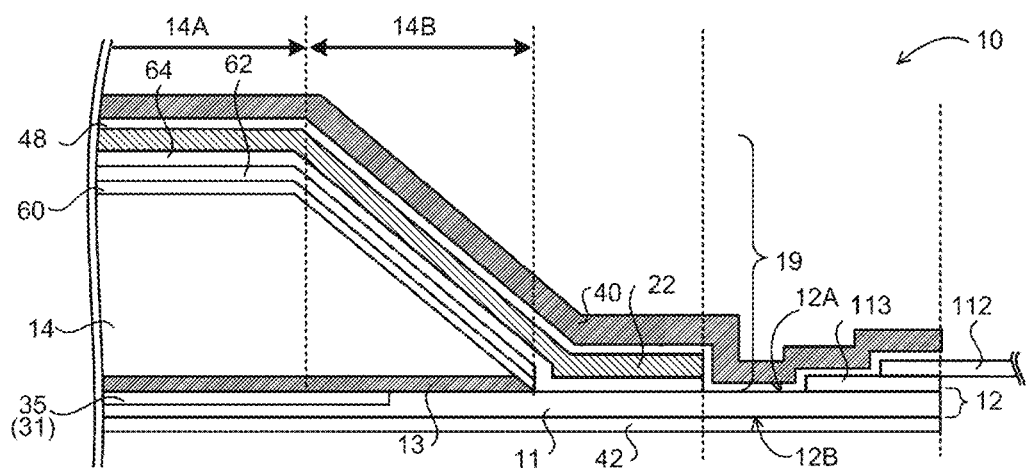
FIG. 27 is a cross-section illustrating an example of configuration of a radiation detector of an exemplary embodiment of technology disclosed herein.

In the example illustrated in FIG. 27, the outer peripheral portion of the reinforcement substrate 40 is angled so as to follow the slope of the peripheral edge portion 14B of the conversion layer 14, and covers a portion where the bonding layer 64 and the protective layer 22 cover over the TFT substrate 12, a portion on top of the substrate at the outer side thereof, and the connection portions between the flexible cable 112 and the terminals 113. The portions of the reinforcement substrate 40 extending over the TFT substrate 12 and over the flexible cable 112 are respectively bonded to the TFT substrate 12 and the flexible cable 112 through the adhesion layer 48. The connection portions between the flexible cable 112 and the terminals 113 are covered by the bent reinforcement substrate 40, enabling detachment of the flexible cable 112 to be suppressed. Moreover, since the other end of the flexible cable 112 is anticipated to be connected to a control board mounted with electronic components, there is a concern regarding comparatively large bending of the TFT substrate 12 occurring at the connection portions between the flexible cable 112 and the terminals 113. Since the connection portions between the flexible cable 112 and the terminals 113 are covered by the reinforcement substrate 40, such bending of the TFT substrate 12 at these portions can be suppressed.

Figure 28:
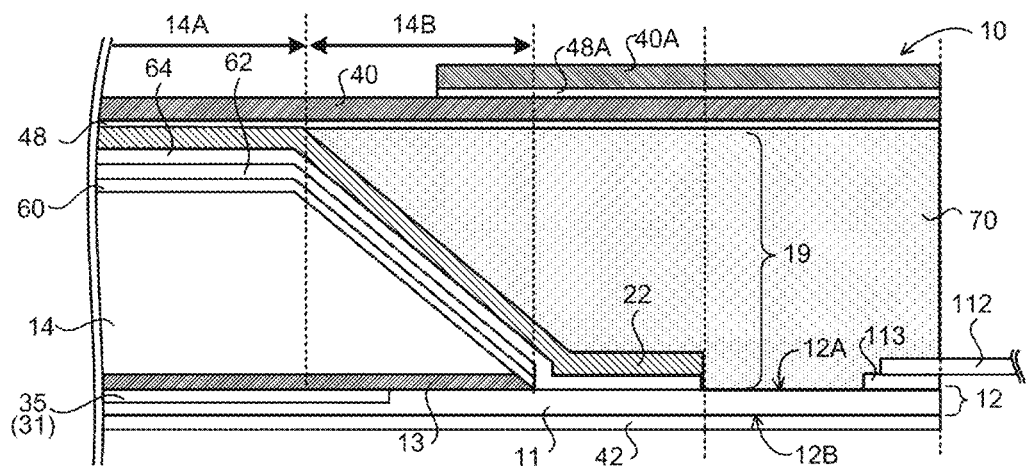
FIG. 28 is a cross-section illustrating an example of configuration of a radiation detector of an exemplary embodiment of technology disclosed herein.

In the example illustrated in FIG. 28, a space formed between the conversion layer 14 (the protective layer 22) and the reinforcement substrate 40, and between the TFT substrate 12 and the reinforcement substrate 40, is filled with the filler 70. Moreover, an additional and separate bending reinforcement substrate 40A is stacked on the front surface of the reinforcement substrate 40 at the region corresponding to the end portion of the conversion layer 14, with the adhesion layer 48A interposed therebetween. More specifically, the reinforcement substrate 40A is provided at a region straddling the end portion (outer edge, edge) of the conversion layer 14. The reinforcement substrate 40A may be configured from the same materials as the reinforcement substrate 40. In the radiation detector 10, the amount of bending of the TFT substrate 12 is comparatively large at the end portion of the conversion layer 14. Forming a multi-layer structure using the reinforcement substrates 40 and 40A at the region corresponding to the end portion of the conversion layer 14 enables the effect of suppressing bending of the TFT substrate 12 to be enhanced at the end portion of the conversion layer 14.

As illustrated in FIG. 29 to FIG. 33, the end portion of the reinforcement substrate 40 may be provided so as to be positioned at the outer side of the end portion of the TFT substrate 12.

Figure 29:
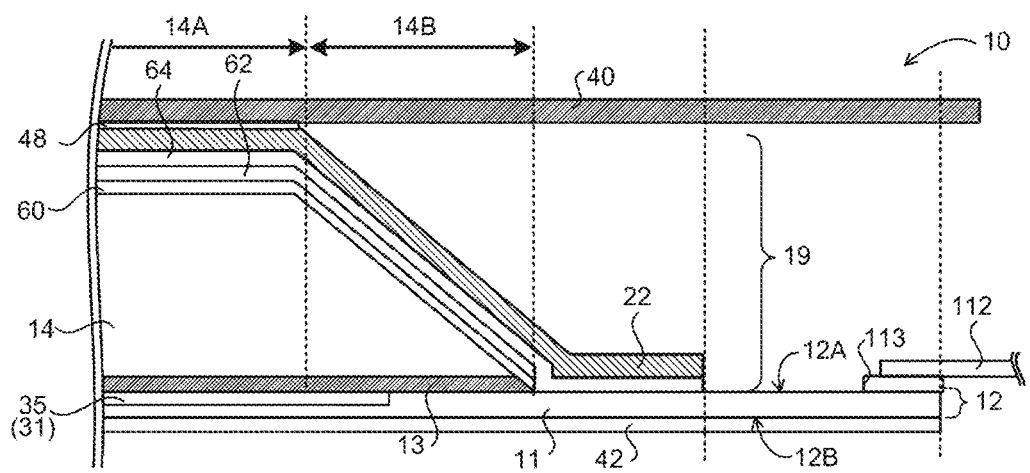
FIG. 29 is a cross-section illustrating an example of configuration of a radiation detector of an exemplary embodiment of technology disclosed herein.

In the example illustrated in FIG. 29, the reinforcement substrate 40 is bonded to the protective layer 22 through the adhesion layer 48 at the region corresponding to the central portion 14A of the conversion layer 14. A space corresponding to the slope of the peripheral edge portion 14B of the conversion layer 14 is formed between the conversion layer 14 (the protective layer 22) and the reinforcement substrate 40, and between the TFT substrate 12 and the reinforcement substrate 40, at the region corresponding to the peripheral edge portion 14B of the conversion layer 14 and also at the region at the outer side thereof.

Figure 30:
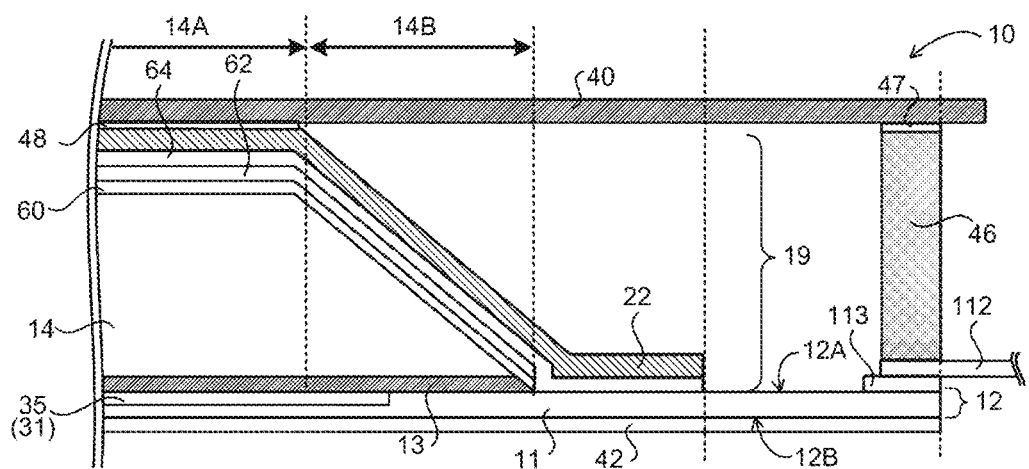
FIG. 30 is a cross-section illustrating an example of configuration of a radiation detector of an exemplary embodiment of technology disclosed herein.

In the example illustrated in FIG. 30, the end portion of the reinforcement substrate 40 is supported by the spacer 46. Namely, one end of the spacer 46 is connected to the flexible cable 112 provided at the end portion of the TFT substrate 12, and the other end of the spacer 46 is connected to the end portion of the reinforcement substrate 40 through the bonding layer 47. By using the spacer 46 to support the end portion of the reinforcement substrate 40 that extends so as to form the space between itself and the TFT substrate 12, detachment of the reinforcement substrate 40 can be suppressed. Moreover, the bending suppression effect from the reinforcement substrate 40 can be caused to act as far as the vicinity of the end portion of the TFT substrate 12.

Figure 31:
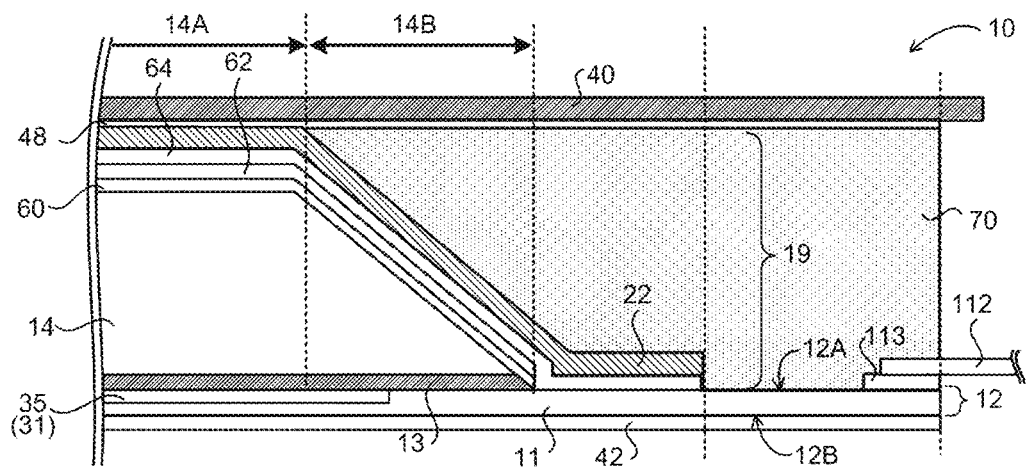
FIG. 31 is a cross-section illustrating an example of configuration of a radiation detector of an exemplary embodiment of technology disclosed herein.

In the example illustrated in FIG. 31, the filler 70 is filled into the space formed between the conversion layer 14 (the protective layer 22) and the reinforcement substrate 40, and between the TFT substrate 12 and the reinforcement substrate 40. In the present exemplary embodiment, the connection portions between the flexible cable 112 and the terminals 113 are covered by the filler 70. By filling the filler 70 into the space formed between the conversion layer 14 (the protective layer 22) and the reinforcement substrate 40 and between the TFT substrate 12 and the reinforcement substrate 40 in this manner, the reinforcement substrate 40 can be better suppressed from detaching from the conversion layer 14 (the protective layer 22) than in the embodiment illustrated in FIG. 29. Furthermore, due to the structure in which the conversion layer 14 is fixed to the TFT substrate 12 by both the reinforcement substrate 40 and the filler 70, the conversion layer 14 can be suppressed from detaching from the TFT substrate 12. Moreover, since the connection portions between the flexible cable 112 and the terminals 113 are covered by the filler 70, detachment of the flexible cable 112 can be suppressed.

Figure 32:
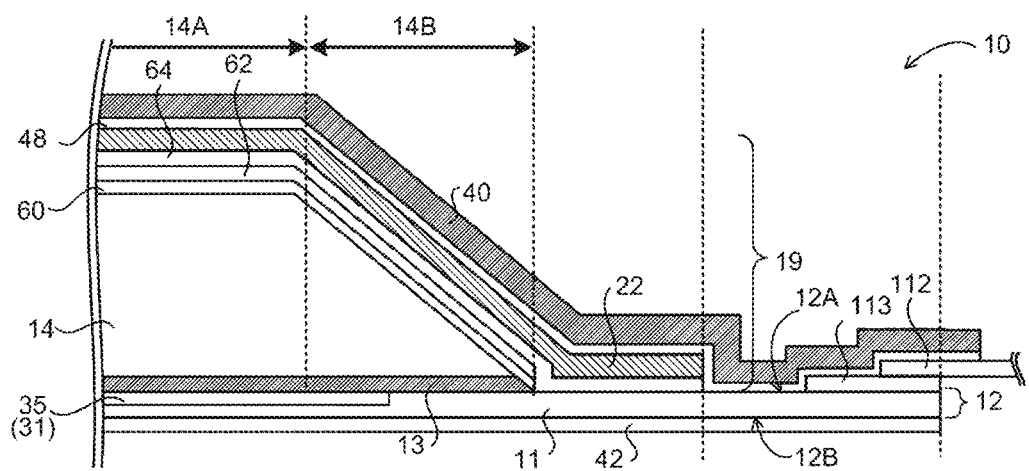
FIG. 32 is a cross-section illustrating an example of configuration of a radiation detector of an exemplary embodiment of technology disclosed herein.

In the example illustrated in FIG. 32, the outer peripheral portion of the reinforcement substrate 40 is angled so as to follow the slope of the peripheral edge portion 14B of the conversion layer 14. The outer peripheral portion of the reinforcement substrate 40 also covers the portion where the bonding layer 64 and the protective layer 22 cover over the TFT substrate 12, the portion on top of the substrate at the outer side thereof, and the connection portions between the flexible cable 112 and the terminals 113. The portions of the reinforcement substrate 40 extending over the TFT substrate 12 and over the flexible cable 112 are respectively bonded to the TFT substrate 12 and the flexible cable 112 through the adhesion layer 48. By covering the connection portions between the flexible cable 112 and the terminals 113 with the reinforcement substrate 40, detachment of the flexible cable 112 can be suppressed. Moreover, since the other end of the flexible cable 112 is anticipated to be connected to a control board mounted with electronic components, there is a concern regarding comparatively large bending of the TFT substrate 12 at the connection portions between the flexible cable 112 and the terminals 113. Since the connection portions between the flexible cable 112 and the terminals 113 are covered by the reinforcement substrate 40, such bending of the TFT substrate 12 at these portions can be suppressed.

Figure 33:
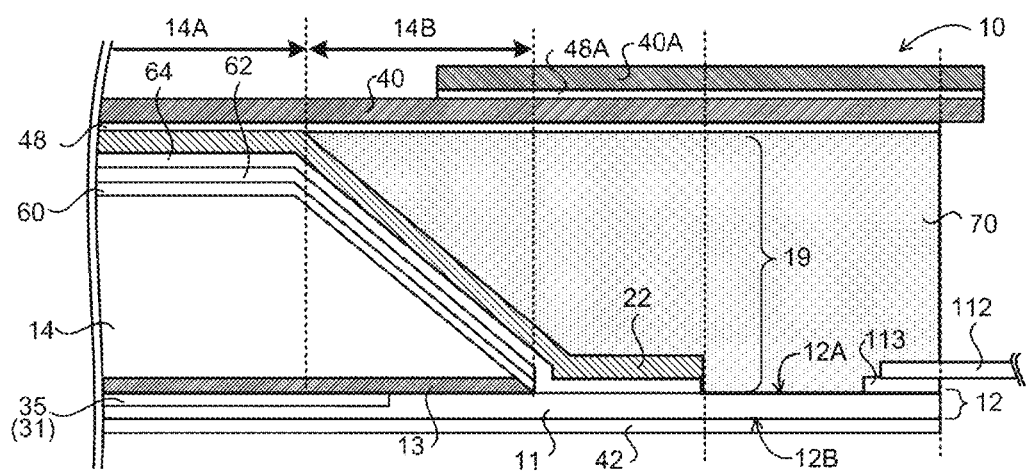
FIG. 33 is a cross-section illustrating an example of configuration of a radiation detector of an exemplary embodiment of technology disclosed herein.
Figure 34:
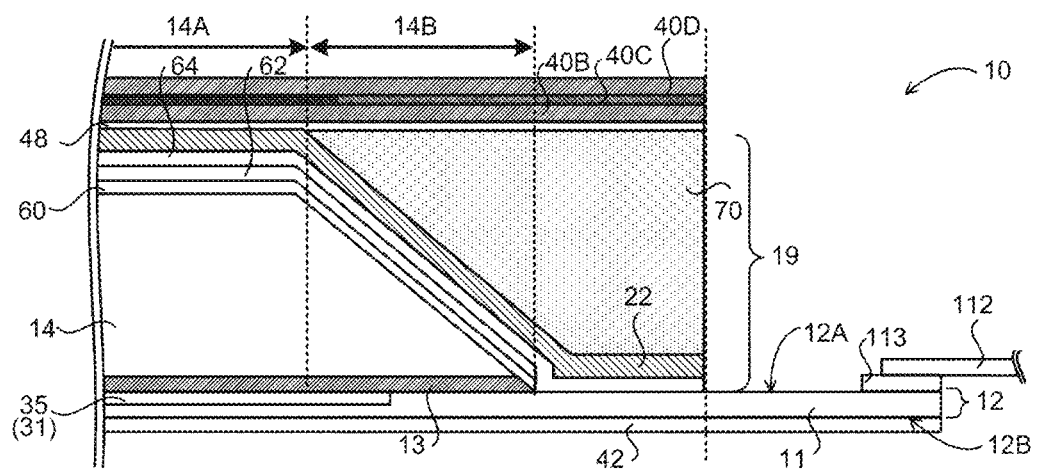
FIG. 34 is a cross-section illustrating an example of configuration of a radiation detector of an exemplary embodiment of technology disclosed herein.

In the example illustrated in FIG. 33, the filler 70 is filled into the space formed between the conversion layer 14 (the protective layer 22) and the reinforcement substrate 40 and between the TFT substrate 12 and the reinforcement substrate 40. Moreover, the additional and separate reinforcement substrate 40A is stacked on the front surface of the reinforcement substrate 40 at the region corresponding to the end portion of the conversion layer 14, with the adhesion layer 48A interposed therebetween. More specifically, the reinforcement substrate 40A is provided at a region straddling the end portion (outer edge, edge) of the conversion layer 14. The reinforcement substrate 40A may be configured from the same materials as the reinforcement substrate 40. In the radiation detector 10, the amount of bending of the TFT substrate 12 is comparatively large at the end portion of the conversion layer 14. Forming a multi-layer structure using the reinforcement substrates 40 and 40A at the region corresponding to the end portion of the conversion layer 14 enables the effect of suppressing bending of the TFT substrate 12 to be enhanced at the end portion of the conversion layer 14.

As described previously, in processes to manufacture the radiation detector 10, the flexible TFT substrate 12 is affixed onto the support body 400, for example a glass substrate. After stacking the conversion layer 14 on top of the TFT substrate 12, the support body 400 is separated from the TFT substrate 12. Bending occurs in the flexible TFT substrate 12 when this is performed, and so there is a concern that the pixels 30 formed on top of the TFT substrate 12 might be damaged thereby. By stacking the reinforcement substrate 40 on top of the conversion layer 14 as in the embodiments illustrated in the examples of FIG. 13 to FIG. 33 prior to separating the support body 400 from the TFT substrate 12, the bending of the TFT substrate 12 that occurs when the support body 400 is being separated from the TFT substrate 12 can be suppressed, enabling the risk of damage to the pixels 30 to be reduced.

Moreover, the reinforcement substrate 40 is not limited to a single layer (one layer), and may be configured with multiple layers. For example, in the radiation detector 10 in the example illustrated in FIG. 34, the reinforcement substrate 40 is a multi-layered film configured of three layers in which a first reinforcement substrate 40B, a second reinforcement substrate 40C, and a third reinforcement substrate 40D are stacked in sequence from the side closest to the conversion layer 14.

In cases in which the reinforcement substrate 40 has multiple layers, each of the layers included in the reinforcement substrate 40 preferably has a different function. For example, in the example illustrated in FIG. 34, the first reinforcement substrate 40B and the third reinforcement substrate 40D may be configured as layers having a non-conductive anti-static function, while the second reinforcement substrate 40C may be configured as a conductive layer such that the reinforcement substrate 40 has an electromagnetic shielding function. In such cases, the first reinforcement substrate 40B and the third reinforcement substrate 40D may employ an anti-static film such as a film employing the anti-static coating COLCOAT (trade name, manufactured by COLCOAT Co., Ltd.). The second reinforcement substrate 40C may employ a conductive sheet, or a conductive mesh sheet made of Cu or the like.

Figure 52:
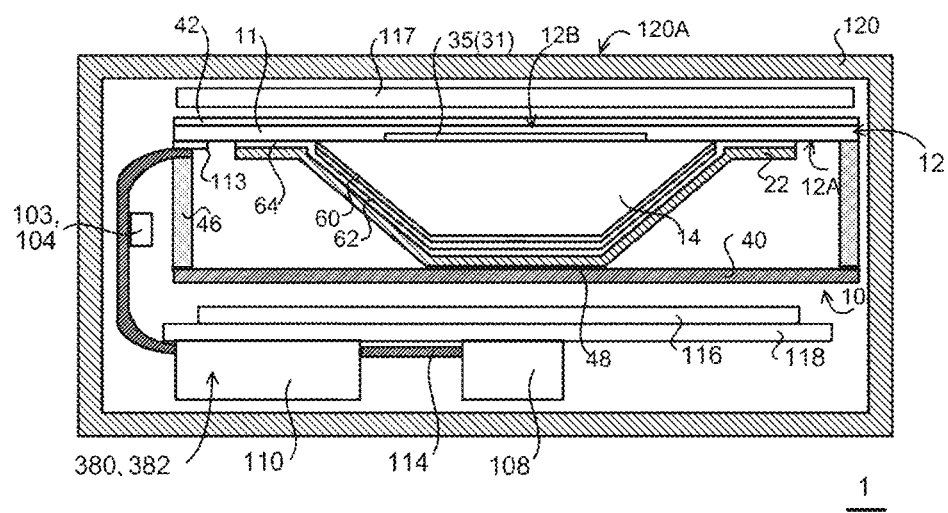
FIG. 52 is a cross-section illustrating an example of configuration of a radiographic imaging device of an exemplary embodiment of technology disclosed herein.

For example, in cases in which the reading approach of the radiation detector 10 is an ISS approach, the control board 110, the power source section 108, and the like may be provided on the conversion layer 14 side (see FIG. 52). Providing the reinforcement substrate 40 with an anti-static function in this manner enables electromagnetic noise from the control board 110 and the power source section 108 to be shielded.

Figure 35:
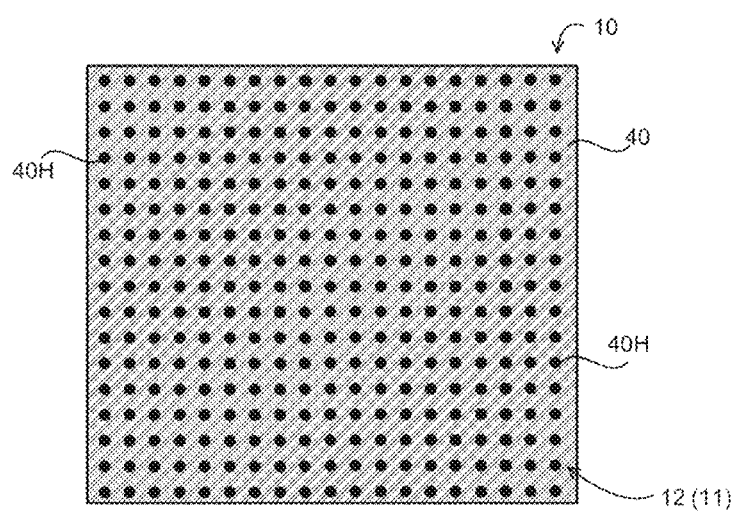
FIG. 35 is a plan view illustrating an example of a structure of a reinforcement member of an exemplary embodiment of technology disclosed herein.

FIG. 35 is a plan view illustrating an example of a structure of the reinforcement substrate 40. A main face of the reinforcement substrate 40 may include plural through holes 40H. The size and pitch of the through holes 40H is prescribed so as to obtain the desired rigidity of the reinforcement substrate 40.

Including the plural through holes 40H in the reinforcement substrate 40 enables air introduced at the joining face of the reinforcement substrate 40 to the conversion layer 14 to escape through the through holes 40H. This enables air bubbles to be suppressed from being generated at the joining face of the reinforcement substrate 40 to the conversion layer 14.

There is a concern that air bubbles might be generated at the joining face if no mechanism is provided to allow air introduced at the joining face of the reinforcement substrate 40 to the conversion layer 14 to escape. For example, were air bubbles generated at the joining face to expand due to heat during operation of the radiographic imaging device 1, there would be a drop in the cohesion between the reinforcement substrate 40 and the conversion layer 14. This would lead to a concern that the bending suppression effect from the reinforcement substrate 40 might not be sufficiently exhibited. By using the reinforcement substrate 40 including the plural through holes 40H as illustrated in FIG. 35, the generation of air bubbles at the joining face of the reinforcement substrate 40 to the conversion layer 14 can be suppressed as described above, enabling the cohesion between the reinforcement substrate 40 and the conversion layer 14 to be maintained. This enables the bending suppression effect of the reinforcement substrate 40 to be maintained.

Figure 36:
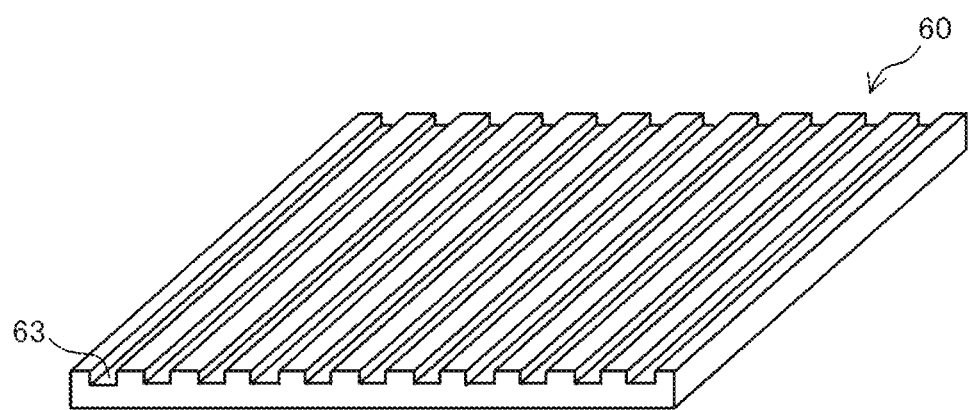
FIG. 36 is a perspective view illustrating an example of a structure of a reinforcement member of an exemplary embodiment of technology disclosed herein.
Figure 37:
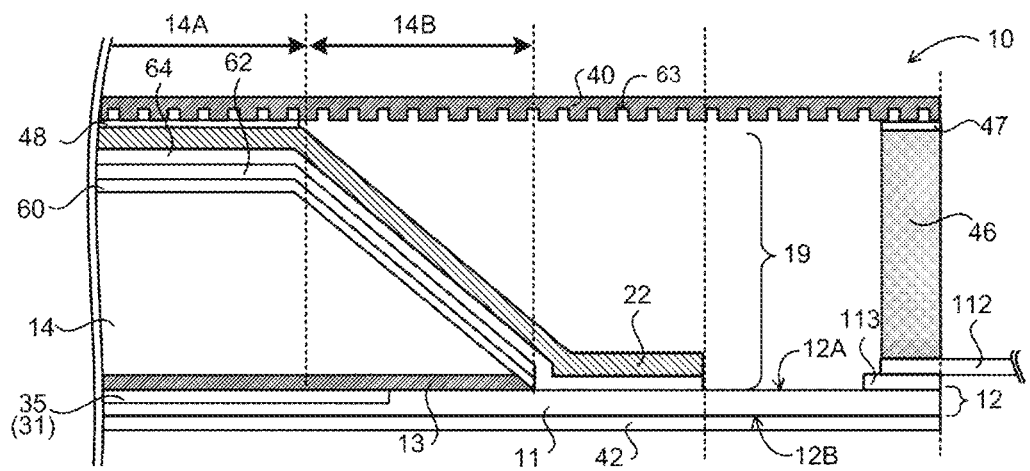
FIG. 37 is a cross-section illustrating an example of configuration of a radiation detector of an exemplary embodiment of technology disclosed herein.

FIG. 36 is a perspective view illustrating another example of the structure of the reinforcement substrate 40. In the example illustrated in FIG. 36, the reinforcement substrate 40 includes an indented-and-protruding structure on the joining face to the conversion layer 14. The indented-and-protruding structure may be configured including plural grooves 63 arranged parallel to each other, as illustrated in FIG. 36. The face of the reinforcement substrate 40 that includes the indented-and-protruding structure configured from the plural grooves 63 is, for example as illustrated in FIG. 37, joined to the conversion layer 14 that has been covered by the reflective layer 62. Due to the reinforcement substrate 40 including the indented-and-protruding structure on the joining face to the conversion layer 14 in this manner, any air introduced to the joining portion of the reinforcement substrate 40 and the conversion layer 14 is able to escape through the grooves 63. Similarly to in the embodiment illustrated in FIG. 35, this accordingly enables the generation of air bubbles at the joining face of the reinforcement substrate 40 to the conversion layer 14 to be suppressed. This enables the cohesion between the reinforcement substrate 40 and the conversion layer 14 to be maintained, and enables the bending suppression effect of the reinforcement substrate 40 to be maintained.

Figure 38:
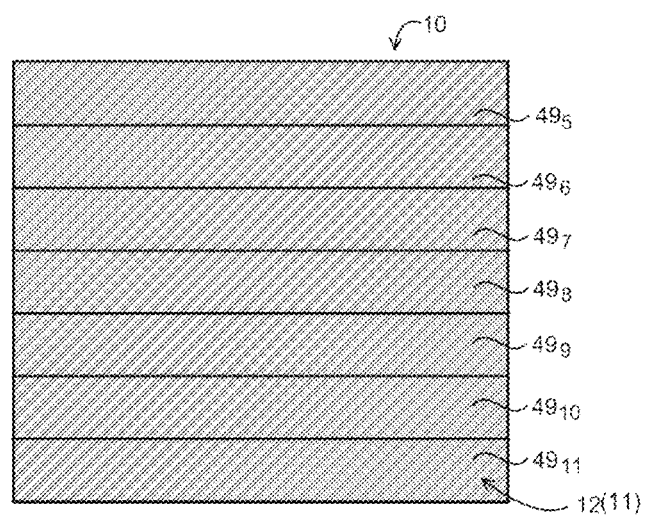
FIG. 38 is a plan view illustrating an example of a structure of a reinforcement member of an exemplary embodiment of technology disclosed herein.
Figure 39:
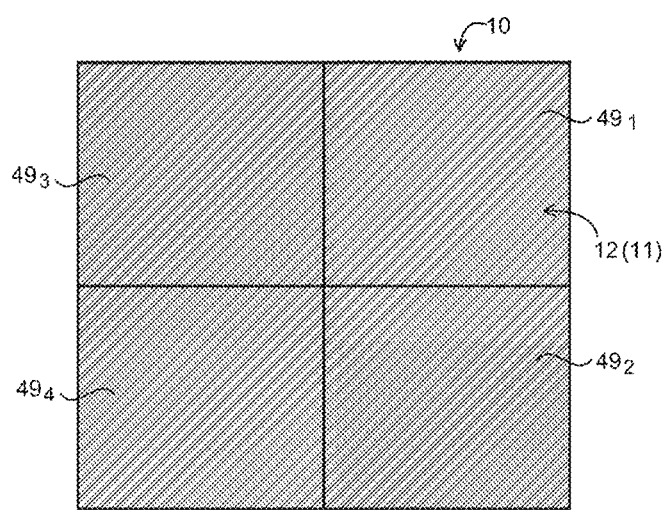
FIG. 39 is a plan view illustrating an example of a structure of a reinforcement member of an exemplary embodiment of technology disclosed herein.
Figure 49:
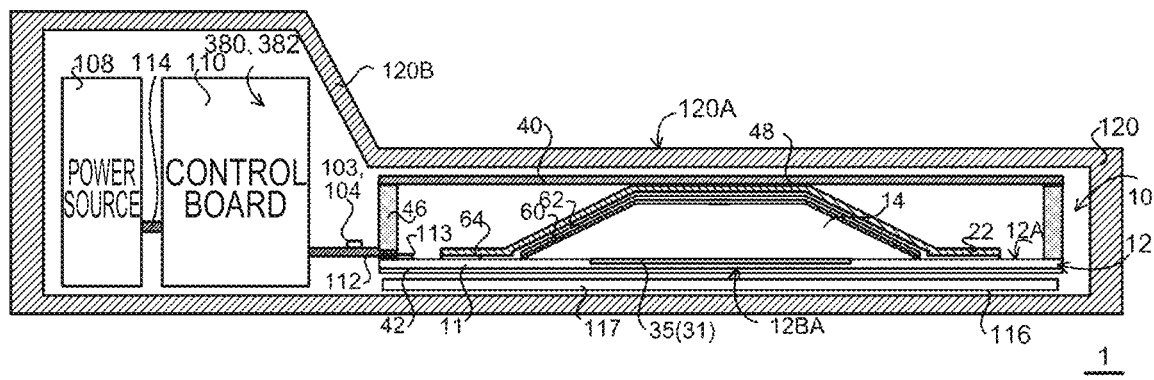
FIG. 49 is a cross-section illustrating an example of configuration of a radiographic imaging device of an exemplary embodiment of technology disclosed herein.
Figure 50:
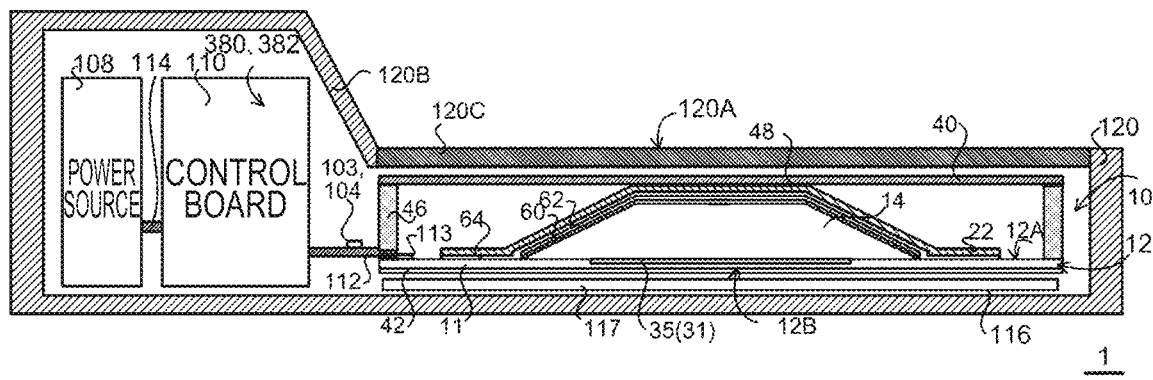
FIG. 50 is a cross-section illustrating an example of configuration of a radiographic imaging device of an exemplary embodiment of technology disclosed herein.

FIG. 38 and FIG. 39 are plan views illustrating other examples of structures of the reinforcement substrate 40. As illustrated in FIG. 38 and FIG. 39, the reinforcement substrate 40 may be segmented into plural pieces 49. The reinforcement substrate 40 may, as illustrated in FIG. 38, be segmented into the plural pieces 49 (FIGS. 49$_5$ to 49$_{11}$) arrayed along one direction. Alternatively, the reinforcement substrate 40 may, as illustrated in FIG. 39, be segmented into the plural pieces 49 (FIGS. 49$_1$ to 49$_4$) arrayed in both a longitudinal direction and a lateral direction.

The greater the surface area of the reinforcement substrate 40, the more readily air bubbles are generated at the joining face of the reinforcement substrate 40 to the conversion layer 14. As illustrated in FIG. 38 and FIG. 39, segmenting the reinforcement substrate 40 into the plural pieces 49 enables the generation of air bubbles at the joining face of the reinforcement substrate 40 to the conversion layer 14 to be suppressed. This enables the cohesion between the reinforcement substrate 40 and the conversion layer 14 to be maintained, and thereby enables the bending suppression effect of the reinforcement substrate 40 to be maintained.

A reinforcement member 51 may be provided on the opposite side of the reinforcement member 41 to the side contacting the TFT substrate 12 (the second surface 12B). FIG. 40 to FIG. 44 are cross-sections respectively illustrating examples of embodiments of installation of the reinforcement member 51.

In the examples illustrated in FIG. 40 to FIG. 44, the reinforcement member 51 is stacked on an opposite-side surface of the reinforcement member 41 to the surface on the TFT substrate 12 side, with a bonding layer 52 interposed therebetween. The reinforcement member 51 may be configured from the same materials as the reinforcement substrate 40. In cases in which the radiation detector 10 employs an ISS approach, the reinforcement member 51 is preferably provided only at an outer peripheral portion of the TFT substrate 12 so as to keep the surface area of locations where the reinforcement member 51 and the pixel region 35 overlap each other as small as possible. Namely, the reinforcement member 51 may have a ring shape with an opening 61 at a location corresponding to the pixel region 35, as illustrated in FIG. 40 to FIG. 44. Forming a multi-layer structure with the reinforcement member 41 and the reinforcement member 51 at the outer peripheral portion of the TFT substrate 12 in this manner enables the rigidity of the outer peripheral portion of the TFT substrate 12 that is comparatively susceptible to bending to be reinforced.

Figure 40:
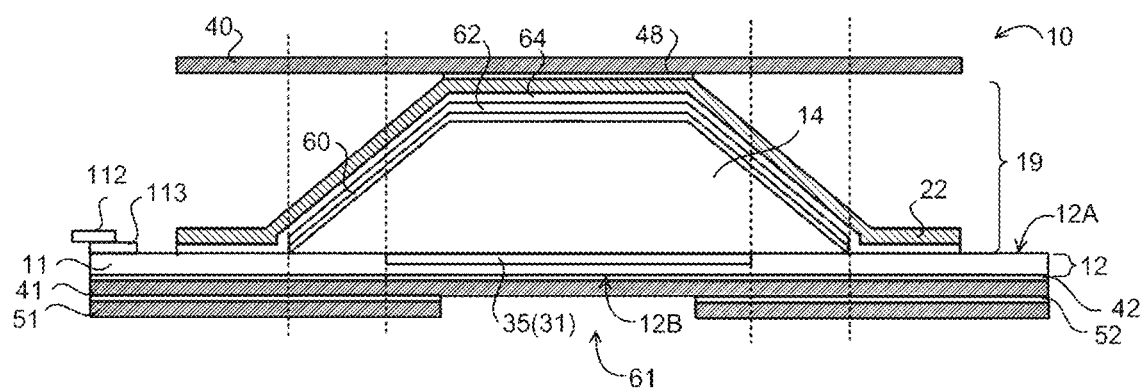
FIG. 40 is a cross-section illustrating an example of configuration of a radiation detector of an exemplary embodiment of technology disclosed herein.
Figure 41:
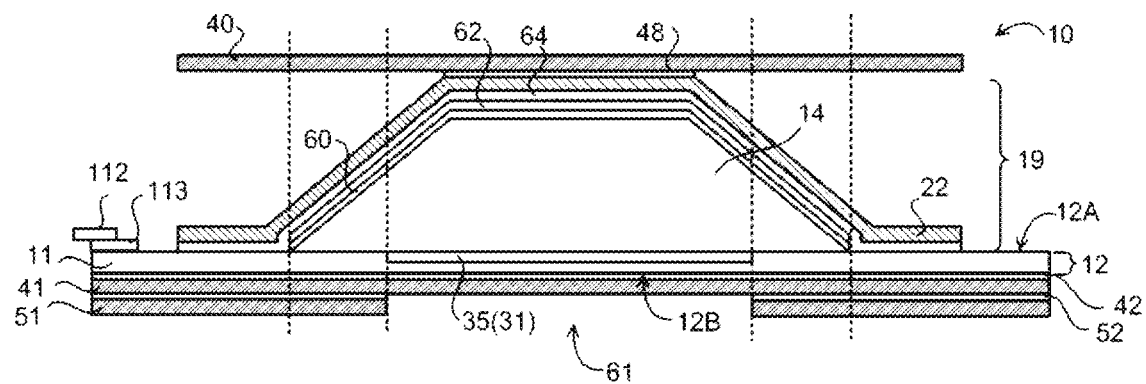
FIG. 41 is a cross-section illustrating an example of configuration of a radiation detector of an exemplary embodiment of technology disclosed herein.
Figure 42:
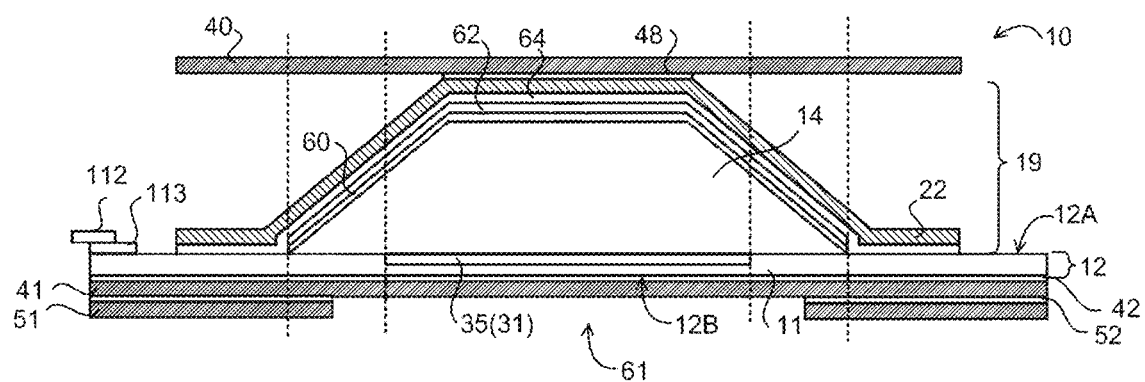
FIG. 42 is a cross-section illustrating an example of configuration of a radiation detector of an exemplary embodiment of technology disclosed herein.

In the examples illustrated in FIG. 40 to FIG. 42, the reinforcement member 51 is provided at a region straddling the end portion (outer edge, edge) of the conversion layer 14. In the radiation detector 10, the amount of bending of the TFT substrate 12 is comparatively large at the end portion of the conversion layer 14. Forming a multi-layer structure using the reinforcement member 41 and the reinforcement member 51 at the region corresponding to the end portion of the conversion layer 14 enables the effect of suppressing bending of the TFT substrate 12 to be enhanced at the end portion of the conversion layer 14.

In cases in which an ISS approach is employed in the radiation detector 10, there is a concern that were a portion of the reinforcement member 51 to overlap with the pixel region 35 as illustrated in FIG. 40, this might have an impact on the images, depending on the material employed in the reinforcement member 51. Thus, in cases in which a portion of the reinforcement member 51 overlaps with the pixel region 35, a plastic is preferably employed for the material of the reinforcement member 51.

As illustrated in FIG. 41 and FIG. 42, an embodiment is most preferably adopted in which the reinforcement member 51 straddles the end portion (outer edge, edge) of the conversion layer 14 but does not overlap with the pixel region 35 (namely, an embodiment in which an edge of the opening 61 in the reinforcement member 51 is disposed at the outer side of the pixel region 35). In the example illustrated in FIG. 41, the position of the edge of the opening 61 in the reinforcement member 51 is substantially aligned with the position of the end portion of the pixel region 35. In the example illustrated in FIG. 42, the edge of the opening 61 in the reinforcement member 51 is disposed between the end portion of the pixel region 35 and the end portion of the conversion layer 14.

Figure 43:
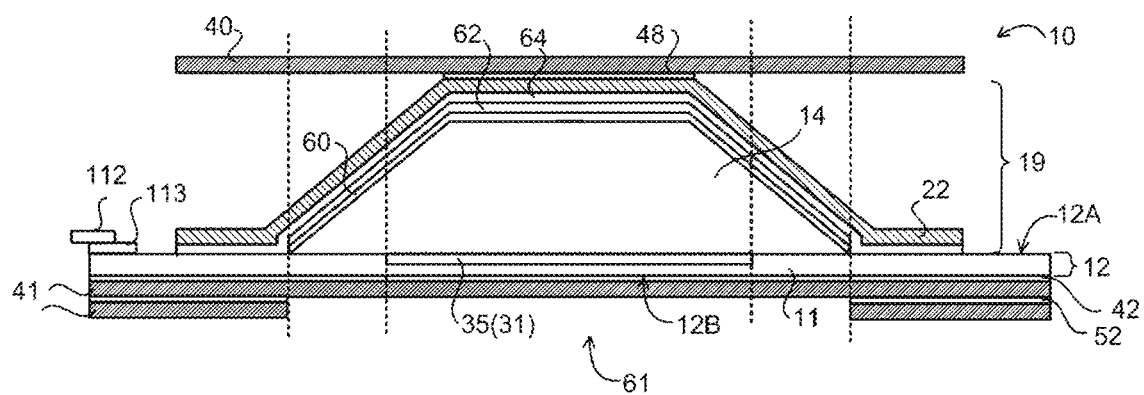
FIG. 43 is a cross-section illustrating an example of configuration of a radiation detector of an exemplary embodiment of technology disclosed herein.
Figure 44:
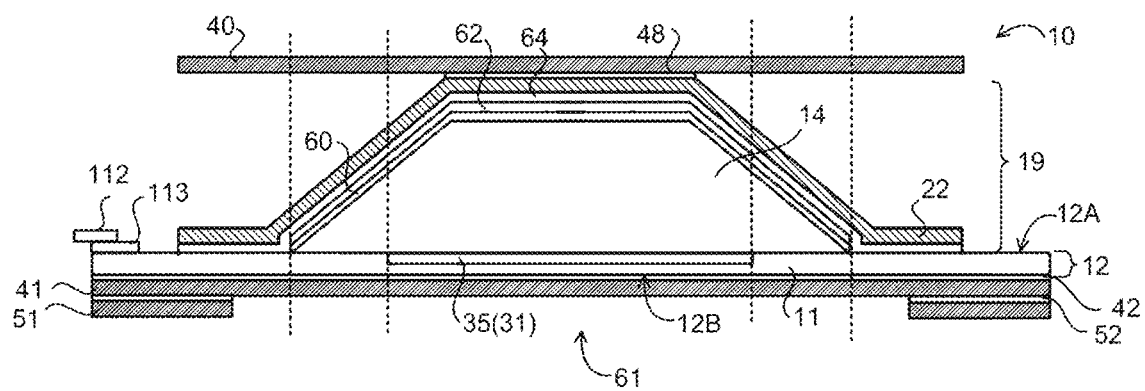
FIG. 44 is a cross-section illustrating an example of configuration of a radiation detector of an exemplary embodiment of technology disclosed herein.

Moreover, the position of the edge of the opening 61 in the reinforcement member 51 may be disposed so as to be substantially aligned with the position of the end portion of the conversion layer 14 as illustrated in FIG. 43, or may be disposed so as to be further toward the outer side than the end portion of the conversion layer 14 as illustrated in FIG. 44. In such cases, there is no structure present where the reinforcement member 51 straddles the end portion (outer edge, edge) of the conversion layer 14, and so there might be a concern regarding a lessening of the effect of suppressing bending of the TFT substrate 12 at the end portion of the conversion layer 14. However, due to forming a stacked structure using the reinforcement member 41 and the reinforcement member 51 at the outer peripheral portion of the TFT substrate 12 where the connection portions between the flexible cable 112 and the terminals 113 are present, the effect of suppressing bending of the TFT substrate 12 at the connection portions between the flexible cable 112 and the terminals 113 is maintained.

In the radiation detectors 10 of the exemplary embodiments described above, explanation has been given regarding embodiments in which the size of the TFT substrate 12 (base member 11) and the size of the reinforcement member 41 are the same as each other. However, the size of the TFT substrate 12 and the size of the reinforcement member 41 may be different to each other.

For example, in cases in which the radiation detector 10 is applied to the radiographic imaging device 1, the radiation detector 10 may be employed fixed to the case 120 (see FIG. 11, etc.) or the like that houses the radiation detector 10. In such cases, as in the example illustrated in FIG. 45A, the reinforcement member 41 may be made larger than the TFT substrate 12 and provided with a flap or the like in order to fix the radiation detector 10 using the location of the flap or the like. For example, an embodiment may be configured in which holes are provided in a flap portion of the reinforcement member 41, and screws are passed through the holes to fix the reinforcement member 41 to the case 120 (see FIG. 11, etc.).

Figure 45A:
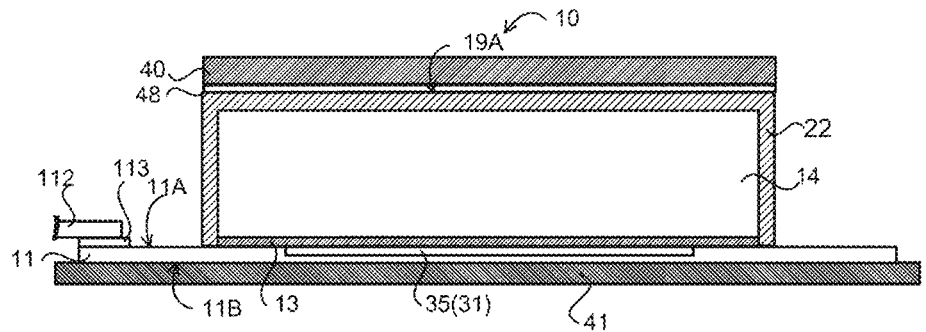
FIG. 45A is a cross-section illustrating an example of configuration of a radiation detector of an exemplary embodiment of technology disclosed herein.
Figure 45B:
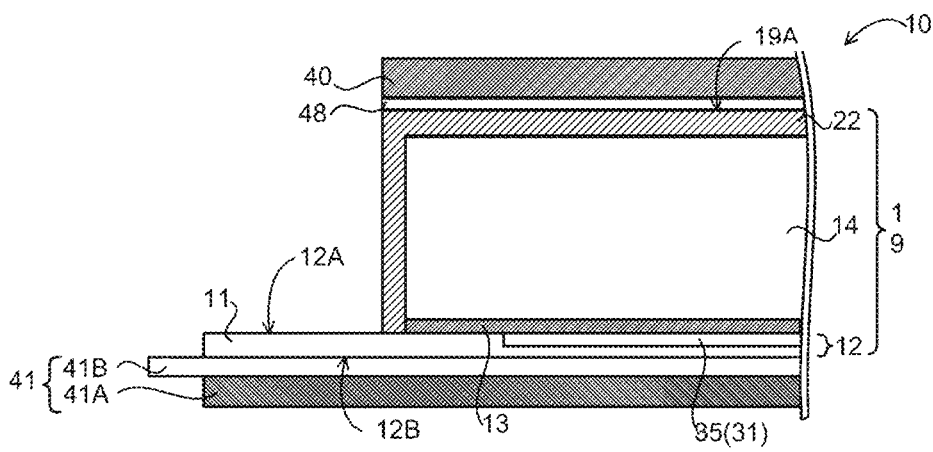
FIG. 45B is a cross-section illustrating an example of configuration of a radiation detector of an exemplary embodiment of technology disclosed herein.

Note that embodiments in which the reinforcement member 41 is larger than the TFT substrate 12 are not limited to the embodiment illustrated in FIG. 45A. An embodiment may be configured in which the reinforcement member 41 is configured with plural stacked layers, with some of these layers being larger than the TFT substrate 12. For example, as illustrated in FIG. 45B, the reinforcement member 41 may be configured with a dual-layer structure including a first layer 41A of similar size to the TFT substrate 12 (the base member 11) and a second layer 41B that is larger than the TFT substrate 12. The first layer 41A is affixed to the second layer 41B using double-sided tape, an adhesion layer, or the like (not illustrated in the drawings). For example, the first layer 41A is preferably formed of similar materials to those of the reinforcement member 41 described above so as to possess similar properties to the reinforcement member 41. The second layer 41B is affixed to the second surface 12B of the base member 11 using double-sided tape, an adhesion layer, or the like (not illustrated in the drawings). For example, ALPET (registered trademark) may be applied as the second layer 41B. In cases in which the reinforcement member 41 is configured with plural layers, conversely to the embodiment illustrated in FIG. 45B, an embodiment may be configured in which the first layer 41A is affixed to the second surface 12B of the base member 11, as illustrated in FIG. 45C.

As described above, in cases in which the radiation detector 10 is fixed to the case 120 (see FIG. 7, etc.) or the like using a flap or the like provided to the reinforcement member 41, such fixing may be performed in a state in which the flap portion is bent. The thinner the thickness thereof, the more easily the flap portion of the reinforcement member 41 will bend, enabling the flap portion alone to be bent without affecting the main body of the radiation detector 10. Accordingly, in cases in which the flap portion or the like is to be bent, an embodiment in which the reinforcement member 41 is configured of plural stacked layers with some of these layers being configured larger than the TFT substrate 12 as illustrated in the examples of FIG. 45B and FIG. 45C is preferable.

Figure 45C:
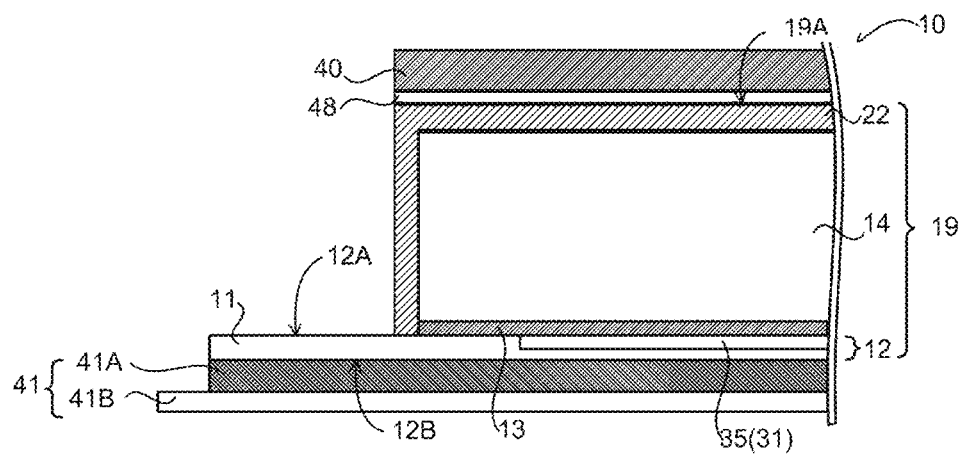
FIG. 45C is a cross-section illustrating an example of configuration of a radiation detector of an exemplary embodiment of technology disclosed herein.
Figure 46:
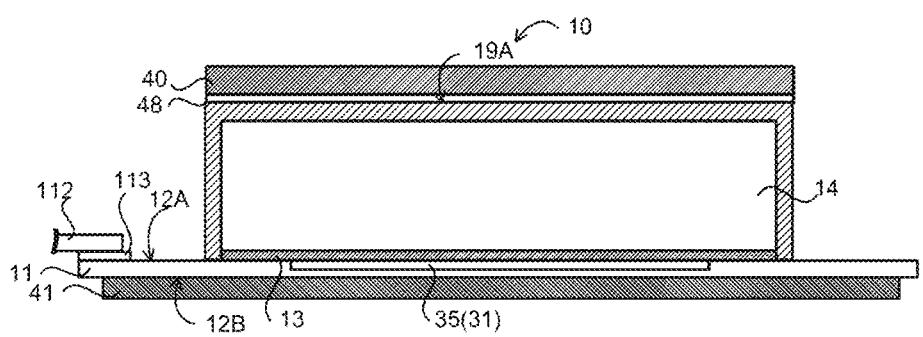
FIG. 46 is a cross-section illustrating an example of configuration of a radiation detector of an exemplary embodiment of technology disclosed herein.

As in the example illustrated in FIG. 46, conversely to the radiation detectors 10 in FIG. 45A to FIG. 45C, the reinforcement member 41 may be smaller than the TFT substrate 12. Positioning an end portion of the TFT substrate 12 at the outer side of an end portion of the reinforcement member 41 facilitates checking of the position of the end portion of the TFT substrate 12 during assembly, for example when housing the radiation detector 10 inside the case 120 (see FIG. 7, etc.), thus enabling positioning precision to be improved. Note that there is no limitation to the embodiment illustrated in FIG. 46, since as long as at least a portion of the end portion of the TFT substrate 12 (the base member 11) is positioned at the outer side of the reinforcement member 41, similar advantageous effects can be obtained and is therefore preferable.

Explanation follows regarding examples of the radiographic imaging device 1 in which the radiation detector 10 is housed inside the case 120, with reference to FIG. 47 to FIG. 53. FIG. 47 to FIG. 53 are diagrams illustrating other configuration examples of the radiographic imaging device 1.

Figure 47:
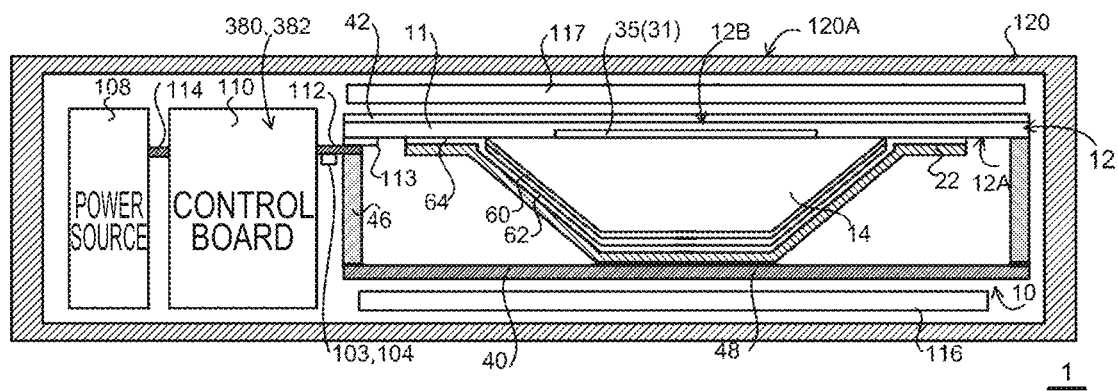
FIG. 47 is a cross-section illustrating an example of configuration of a radiographic imaging device of an exemplary embodiment of technology disclosed herein.
Figure 48:
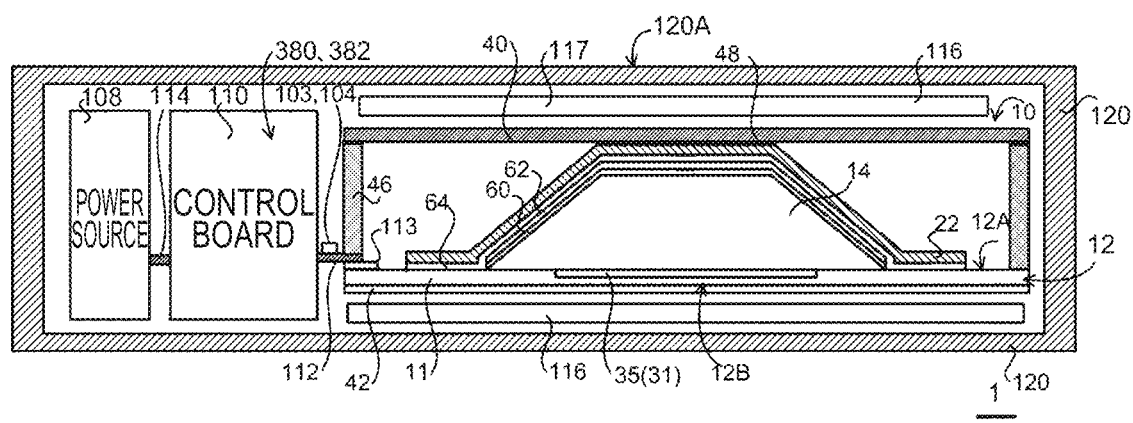
FIG. 48 is a cross-section illustrating an example of configuration of a radiographic imaging device of an exemplary embodiment of technology disclosed herein.

The example illustrated in FIG. 47 is a radiographic imaging device 1 employing an ISS approach, similarly to the radiographic imaging device 1 illustrated in FIG. 11. The example illustrated in FIG. 48 is a radiographic imaging device 1 employing a PSS approach. In the examples illustrated in FIG. 47 and FIG. 48, the radiation detector 10, the control board 110, and the power source section 108 are arranged alongside one another in the lateral direction of the respective drawings.

Note that FIG. 47 and FIG. 48 illustrate embodiments in which both the power source section 108 and the control board 110 are provided on one side of the radiation detector 10, specifically on the side of one edge of the rectangular pixel region 35. However, the positions at which the power source section 108 and the control board 110 are provided are not limited to those of the embodiments illustrated in FIG. 47 and FIG. 48. For example, the power source section 108 and the control board 110 may be provided distributed between two opposing edges of the pixel region 35, or may be provided distributed between two adjacent edges of the pixel region 35.

As in the examples illustrated in FIG. 47 and FIG. 48, in cases in which the radiation detector 10, the control board 110, and the power source section 108 are arranged in a direction intersecting the direction in which the TFT substrate 12 and the conversion layer 14 are stacked, the thickness of the case 120 may be varied between the locations of the case 120 where the power source section 108 and the control board 110 are respectively provided, and the location of the case 120 where the radiation detector 10 is provided.

The power source section 108 and the control board 110 are often each thicker than the radiation detector 10, as in the example illustrated in FIG. 48. In such cases, as in the example illustrated in FIG. 49, the thickness of the location of the case 120 where the radiation detector 10 is provided may be less than the thickness of the locations of the case 120 where the power source section 108 and the control board 110 are provided. In cases in which the thickness is varied between the locations of the case 120 where the power source section 108 and the control board 110 are respectively provided and the location of the case 120 where the radiation detector 10 is provided in this manner, since there might be a concern of causing discomfort or the like to the imaging subject who touches a boundary 120B where a step is created at a boundary between these locations, the boundary 120B is preferably provided with a slope.

So doing enables an ultra-thin portable electronic cassette to be configured according to the thickness of the radiation detector 10.

As another example, in such cases, the case 120 may be configured of different materials at the locations of the case 120 where the power source section 108 and the control board 110 are provided and the location of the case 120 where the radiation detector 10 is provided. Moreover, for example, the locations of the case 120 where the power source section 108 and the control board 110 are provided and the location of the case 120 where the radiation detector 10 is provided may be configured separately to each other.

Moreover, as described previously, the case 120 preferably has a low absorption ratio of the radiation R, in particular X-rays, and high rigidity, and is preferably configured from a material that has a sufficiently high elastic modulus. However, as in the example illustrated in FIG. 50, a location 120C of the case 120 corresponding to the imaging face 120A may be configured with a low absorption ratio of the radiation R and high rigidity, and be configured from a material that has a sufficiently high elastic modulus, while other locations of the case 120 are configured from a different material than the location 120C, for example a material having a lower elastic modulus than the location 120C.

Figure 51:
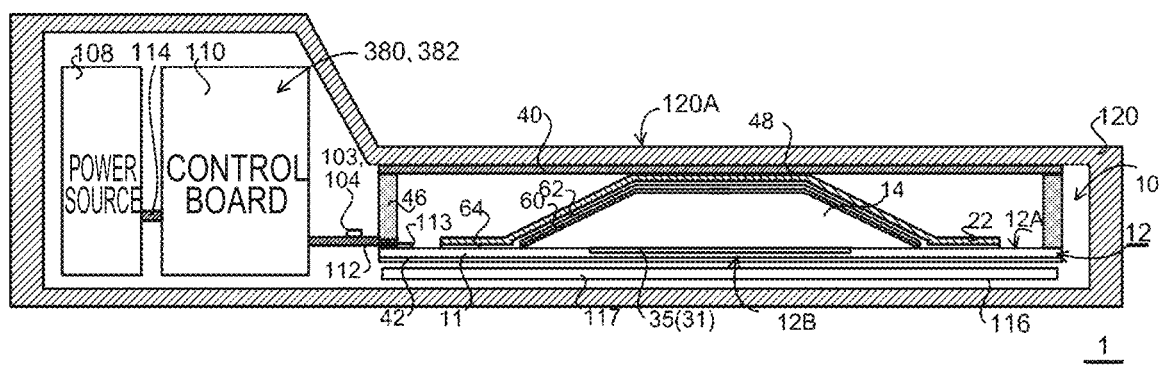
FIG. 51 is a cross-section illustrating an example of configuration of a radiographic imaging device of an exemplary embodiment of technology disclosed herein.

Alternatively, the radiation detector 10 and an inner wall face of the case 120 may contact each other as in the example illustrated in FIG. 51. In such cases, the radiation detector 10 and the inner wall face of the case 120 may be bonded through a bonding layer, or may simply be in contact with each other without providing a bonding layer. Such contact between the radiation detector 10 and the inner wall face of the case 120 further secures the rigidity of the radiation detector 10.

Figure 53:
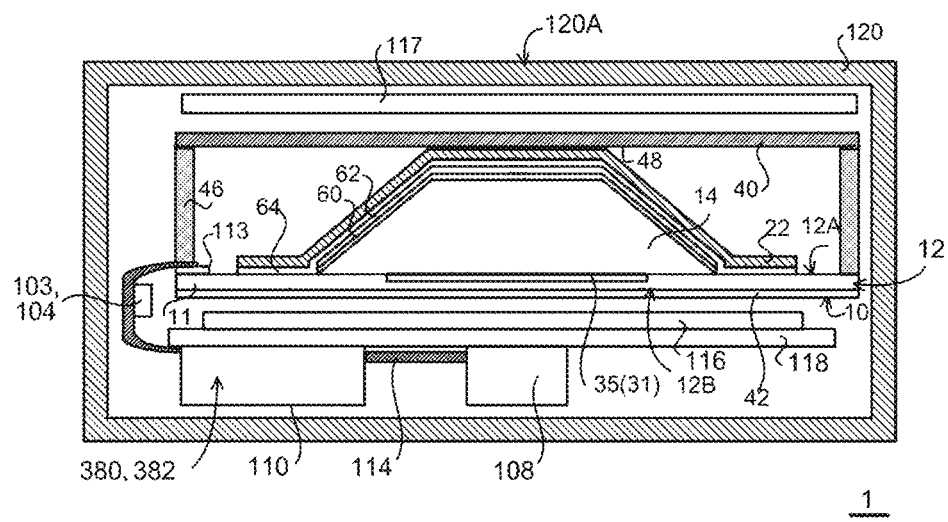
FIG. 53 is a cross-section illustrating an example of configuration of a radiographic imaging device of an exemplary embodiment of technology disclosed herein.

FIG. 52 illustrates an example of a radiographic imaging device 1 employing an ISS approach, similarly to the radiographic imaging device 1 illustrated in FIG. 12. FIG. 53 illustrates an example of a radiographic imaging device 1 employing a PSS approach. In the examples illustrated in FIG. 52 and FIG. 53, the TFT substrate 12 is provided on one side, and the control board 110 and the power source section 108 are provided on the other side of the sheet 116 and the base 118. This configuration enables the size of the radiographic imaging device 1 in plan view to be reduced in comparison to cases in which the radiation detector 10, the control board 110, and the power source section 108 are arranged in the lateral direction in the drawings (see FIG. 47 to FIG. 51).

The disclosures of Japanese Patent Application Nos. 2018-051690, 2018-219696, 2019-022148, 2018-182730, and 2019-022149 are incorporated in their entirety by reference herein.

All cited documents, patent applications, and technical standards mentioned in the present specification are incorporated by reference in the present specification to the same extent as if each individual cited document, patent application, or technical standard was specifically and individually indicated to be incorporated by reference.

What is claimed is:

1. A radiation detector comprising:
   a substrate formed with a plurality of pixels in a pixel region of a flexible base member, the plurality of pixels accumulates charges generated in response to light converted from radiation;
   a conversion layer provided at a surface to which the pixel region is provided on the base member, the conversion layer converts the radiation into light; and
   a reinforcement substrate provided at a surface of the conversion layer that opposes a first surface of the conversion layer to which the substrate is provided, the reinforcement substrate contains a material having a yield point and has a higher rigidity than the base member.

2. The radiation detector of claim 1, wherein the reinforcement substrate is provided at a region that is wider than a region provided with the conversion layer.

3. The radiation detector of claim 2, further comprising a reinforcement member at a surface of the substrate that faces a surface to which the plurality of pixels are formed, the reinforcement member having a higher rigidity than the base member.

4. The radiation detector of claim 2, wherein the reinforcement substrate has a bending elastic modulus of from 1000 MPa to 2500 MPa.

5. The radiation detector of claim 1, wherein:
   the substrate includes a connection region in a region at an outer periphery of a surface to which the plurality of pixels are formed, the connection region being connected with another end of flexible wiring which is connected with a circuit section for reading the charges accumulated in the plurality of pixels; and
   the reinforcement substrate is provided in a region covering the conversion layer and at least a portion of the connection region.

6. The radiation detector of claim 5, further comprising a reinforcement member at a surface of the substrate that faces a surface to which the plurality of pixels are formed, the reinforcement member having a higher rigidity than the base member.

7. The radiation detector of claim 6, wherein the conversion layer includes columnar crystals of CsI.

8. The radiation detector of claim 3, wherein the reinforcement substrate has a bending elastic modulus of from 1000 MPa to 2500 MPa.

9. The radiation detector of claim 1, further comprising a reinforcement member at a surface of the substrate that faces a surface to which the plurality of pixels are formed, the reinforcement member having a higher rigidity than the base member.

10. The radiation detector of claim 4, wherein the reinforcement substrate has a bending elastic modulus of from 1000 MPa to 2500 MPa.

11. The radiation detector of claim 1, further comprising a buffer layer provided between the substrate and the conversion layer.

12. The radiation detector of claim 1, wherein the reinforcement substrate has a bending elastic modulus of from 1000 MPa to 2500 MPa.

13. The radiation detector of claim 1, wherein the material having a yield point is at least one material out of polycarbonate or polyethylene terephthalate.

14. The radiation detector of claim 1, wherein a ratio of a coefficient of thermal expansion of the reinforcement substrate with respect to a coefficient of thermal expansion of the conversion layer is from 0.5 to 2.

15. The radiation detector of claim 1, wherein the reinforcement substrate has a coefficient of thermal expansion of from 30 ppm/K to 80 ppm/K.

16. The radiation detector of claim 1, wherein the conversion layer includes columnar crystals of CsI.

17. The radiation detector of claim 1, wherein the plurality of pixels are formed in the pixel region by a direct formation method.

18. A radiographic imaging device comprising:
the radiation detector of claim 1;
a control section that outputs a control signal for reading the charges accumulated in the plurality of pixels; and
a circuit section electrically connected to the radiation detector by flexible wiring, circuit section reads out charges from the plurality of pixels in response to the control signal.

19. A manufacturing method for a radiation detector, comprising:
a process of coating an adhesion layer onto a reinforcement substrate having a size according to the size of a radiation detector;
a process of forming a substrate by providing a flexible base member to a support body with a separation layer interposed between the base member and the support body, and providing a plurality of pixels in a pixel region of the base member, the plurality of pixels accumulates charges generated in response to light converted from radiation;
a process of forming a conversion layer that converts the radiation into light at a surface to which the pixel region of the base member is provided;
a process of affixing a reinforcement substrate at a surface of the conversion layer that opposes a first surface of the conversion layer to which the substrate is provided, the reinforcement substrate containing a material having a yield point and having a higher rigidity than the base member; and
a process of separating the substrate provided with the conversion layer and the reinforcement substrate from the support body.

20. The radiation detector manufacturing method of claim 19, further comprising, prior to the process of affixing the reinforcement substrate, a process of connecting one end of flexible wiring, which is connected to a circuit section that reads out the charges accumulated in the plurality of pixels, to the substrate.

* * * * *